(12) United States Patent
Jeanguenat et al.

(10) Patent No.: US 7,612,018 B2
(45) Date of Patent: Nov. 3, 2009

(54) INSECTICIDES

(75) Inventors: Andre Jeanguenat, Basel (CH); Anthony Cornelius O'Sullivan, Basel (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 425 days.

(21) Appl. No.: 11/575,436

(22) PCT Filed: Sep. 20, 2005

(86) PCT No.: PCT/EP2005/010145
§ 371 (c)(1), (2), (4) Date: Mar. 16, 2007

(87) PCT Pub. No.: WO2006/032462
PCT Pub. Date: Mar. 30, 2006

(65) Prior Publication Data
US 2008/0214393 A1 Sep. 4, 2008

(30) Foreign Application Priority Data
Sep. 21, 2004 (GB) .................. 0420966.4
Nov. 26, 2004 (GB) .................. 0426041.0

(51) Int. Cl.
*A01N 33/08* (2006.01)
*C07C 221/00* (2006.01)
(52) U.S. Cl. .............. 504/326; 564/305; 564/336; 564/342; 504/189
(58) Field of Classification Search .......... 564/305, 564/336, 342; 504/189, 326
See application file for complete search history.

(56) References Cited

U.S. PATENT DOCUMENTS

| 6,603,044 B1 * | 8/2003 | Tohnishi et al. ............. 564/154 |
| 7,161,032 B2 * | 1/2007 | Yamaguchi et al. .......... 564/84 |
| 2004/0097595 A1 | 5/2004 | Nakao et al. |

FOREIGN PATENT DOCUMENTS

| EP | 1006107 | 6/2000 |
| WO | 2004018415 | 3/2004 |

\* cited by examiner

*Primary Examiner*—Golam M Shameem
(74) *Attorney, Agent, or Firm*—James Cueva

(57) ABSTRACT

Compounds of formula (I) wherein the substituents are as defined in claim 1, and the agrochemically acceptable salts and all stereoisomers and tautomeric forms of the compounds of formula I can be used as agrochemical active ingredients and can be prepared in a manner known per se.

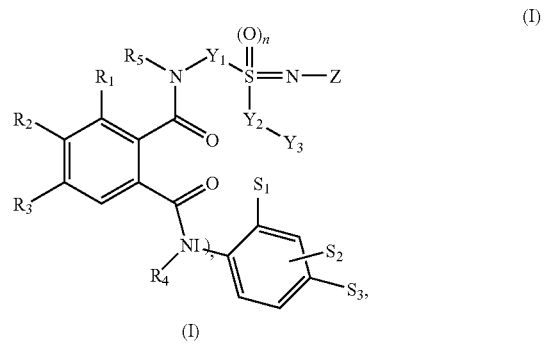

8 Claims, No Drawings

INSECTICIDES

This application is a 371 of International Application No. PCT/EP2005/010145 filed Sep. 20, 2005, which claims priority to GB 0420966.4 filed Sep. 21, 2004, and GB 0426041.0 filed Nov. 26, 2004, the contents of which are incorporated herein by reference.

The present invention relates to phthalamide derivatives, to processes for their preparation, to compositions comprising those compounds, and to their use for controlling insects or representatives of the order Acarina.

Phthalamide derivatives with insecticidal properties are known and described, for example, in EP-A-1006107 and US 2004/0097595 A1. The biological properties of these known compounds, however, are not always fully satisfactory in the field of pest control, which is why there is a need to develop further compounds with pesticidal properties, especially for the control of insects and members of the order Acarina.

There have now been found novel phthalamide derivatives with pesticidal properties. The present invention accordingly relates to compounds of formula I

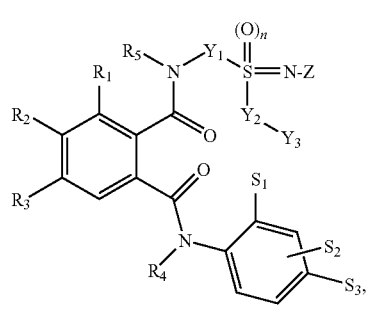

wherein
n is 0 or 1;
$R_1$ is halogen, cyano, $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylsulfonyloxy, $C_1$-$C_8$haloalkylsulfonyloxy or —$OSO_2F$;

each of $R_2$ and $R_3$, which may be the same or different, represents hydrogen, halogen, cyano, $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylsulfonyloxy, $C_1$-$C_8$haloalkylsulfonyloxy, —$OSO_2F$; or $R_2$ together with $R_3$ form a $C_2$-$C_6$alkylene or $C_3$-$C_6$alkenylene bridge which may be interrupted by nitrogene, oxygene and/or —C(O)—, or by —$S(O)_m$—;
and said bridge may be mono- or poly-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, amino, hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano, nitro and/or phenyl, it being possible for the phenyl group in turn to be substituted by hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano or nitro, and the substituents at the nitrogen atom in said bridge being other than halogen, and two oxygen atoms not being located next to one another;

m is 0, 1 or 2;
each of $S_1$ and $S_2$, which may be the same or different, represents hydrogen, halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkenyl, $C_2$-$C_8$haloalkenyl, $C_1$-$C_8$alkynyl, $C_2$-$C_8$haloalkynyl, $C_3$-$C_6$cycloalkyl, $C_3$-$C_6$halocycloalkyl, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_6$alkylamino or di-($C_1$-$C_6$alkyl)amino, whose $C_1$-$C_6$alkyl groups may be the same or different;

$S_3$ is cyano, $C_1$-$C_6$alkyl, halo-$C_1$-$C_6$alkyl, $C_1$-$C_6$alkoxy, halo-$C_1$-$C_6$alkoxy, halo-$C_1$-$C_6$alkoxyhalo-$C_1$-$C_6$alkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl or $C_1$-$C_8$haloalkylsulfonyl; or $S_3$ is a three- to ten-membered monocyclic or fused bicyclic ring system which can be aromatic, partially saturated or fully saturated and can contain 1 to 4 hetero atoms selected from the group consisting of nitrogen, oxygen and sulfur, the ring system being bonded to the phenyl ring directly or via a —O—, —S—, $C_1$-$C_4$alkylene, —CH=CH—, —C≡C—, —$CH_2O$—, —$CH_2N(C_1$-$C_4$alkyl)-, —$CH_2SO$—, or —$CH_2SO_2$ group and it not being possible for each ring system to contain more than 2 oxygen atoms and not more than 2 sulfur atoms, and it being possible for the ring system itself to be mono-, di- or trisubstituted by $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di-($C_1$-$C_2$alkyl)aminosulfonyl, di-($C_1$-$C_4$alkyl)amino, halogen, cyano, nitro, phenyl and benzylthio, it being possible for phenyl and benzylthio, in turn, to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or nitro, and substituents on the nitrogen in the heterocyclic ring being other than halogen;
each of $R_4$ and $R_5$, which may be the same or different, represents hydrogen, $C_1$-$C_6$alkyl, $C_3$-$C_6$alkenyl or $C_3$-$C_6$alkynyl;

$Y_1$ is a $C_1$-$C_6$alkylene, $C_2$-$C_6$alkenylene or $C_3$-$C_6$alkynylene chain which may be mono-, di- or trisubstituted by $R_9$, where the unsaturated bonds of the chain are not attached directly to the sulfur atom; or is $C_3$-$C_6$cycloalkylene, which may be mono-, di- or trisubstituted by $R_{10}$;

$R_9$ and $R_{10}$ independently of one another are halogen, nitro, cyano, hydroxy, $C_1$-$C_6$alkyl, $C_1$-$C_6$haloalkyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkoxycarbonyl, $C_1$-$C_6$alkylcarbonyl, $C_1$-$C_6$alkoxy-$C_1$-$C_6$alkyl, $C_1$-$C_6$alkoxy-$C_1$-$C_6$alkyl, $C_1$-$C_6$alkoxy, $C_1$-$C_6$haloalkoxy, benzyl or phenyl, where phenyl and benzyl for their part may be mono- or polysubstituted by $C_1$-$C_6$alkyl, $C_1$-$C_6$haloalkyl, $C_1$-$C_6$alkoxy, $C_1$-$C_6$haloalkoxy, halogen, cyano, hydroxyl or nitro;

$Y_2$ is a $C_1$-$C_6$alkylene, $C_2$-$C_6$alkenylene or $C_3$-$C_6$alkynylene chain which may be mono-, di- or trisubstituted by $R_{11}$, where the unsaturated bonds of the chain are not attached directly to the sulfur atom; or is $C_3$-$C_6$cycloalkylene, which may be mono-, di- or trisubstituted by $R_{12}$;

$R_{11}$ and $R_{12}$ independently of one another are halogen, nitro, cyano, hydroxy, $C_1$-$C_6$alkyl, $C_1$-$C_6$haloalkyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkoxycarbonyl, $C_1$-$C_6$alkylcarbonyl, $C_1$-$C_6$alkoxy-$C_1$-$C_6$alkyl, $C_1$-$C_6$alkoxy-$C_1$-$C_6$alkyl, $C_1$-$C_6$alkoxy, $C_1$-$C_6$haloalkoxy, benzyl or phenyl, where phenyl and benzyl for their part may be mono-, di- or trisubstituted by $C_1$-$C_6$alkyl, $C_1$-$C_6$haloalkyl, $C_1$-$C_6$alkoxy, $C_1$-$C_6$haloalkoxy, halogen, cyano, hydroxyl or nitro;

$Y_3$ is hydrogen or $C_1$-$C_6$alkyl;

Z is hydrogen, $C_1$-$C_6$alkyl, $C_1$-$C_6$haloalkyl, $C_1$-$C_6$cycloalkyl, $C_1$-$C_6$halocycloalkyl, $C_1$-$C_6$alkylthio, $C_1$-$C_6$haloalkylthio or $C_1$-$C_6$alkoxy-$C_1$-$C_6$alkyl; or $C_1$-$C_6$alkyl, $C_1$-$C_6$haloalkyl, $C_1$-$C_6$cycloalkyl, $C_1$-$C_6$halocycloalkyl, $C_1$-$C_6$alkylthio, $C_1$-$C_6$haloalkylthio or $C_1$-$C_6$alkoxy-$C_1$-$C_6$alkyl substituted by $C_1$-$C_6$alkyl, $C_1$-$C_6$haloalkyl, $C_1$-$C_6$cycloalkyl, $C_1$-$C_6$halocycloalkyl, $C_1$-$C_6$alkoxy, or $C_1$-$C_6$haloalkoxy; or Z is —C(O)$R_6$, —C(O)O—$R_7$, —CONR$_{13}$R$_{14}$, —SO$_2$R$_{15}$ or —OP(OR$_{16}$)(OR$_{17}$)—OR$_{18}$;

$R_6$ is $C_1$-$C_6$alkyl, $C_1$-$C_6$haloalkyl, $C_1$-$C_6$cycloalkyl, $C_1$-$C_6$halocycloalkyl, $C_1$-$C_6$alkylthio, $C_1$-$C_6$haloalkylthio, $C_1$-$C_6$alkoxycarbonyl, $C_1$-$C_6$alkylcarbonyl or $C_1$-$C_6$alkoxy-$C_1$-$C_6$alkyl; or $C_1$-$C_6$alkyl, $C_1$-$C_6$haloalkyl, $C_1$-$C_6$cycloalkyl, $C_1$-$C_6$halocycloalkyl, $C_1$-$C_6$alkylthio, $C_1$-$C_6$haloalkylthio, $C_1$-$C_6$alkoxycarbonyl, $C_1$-$C_6$alkylcarbonyl or $C_1$-$C_6$alkoxy-$C_1$-$C_6$alkyl substituted by $C_1$-$C_6$alkyl, $C_1$-$C_6$haloalkyl, $C_1$-$C_6$cycloalkyl, $C_1$-$C_6$halocycloalkyl, $C_1$-$C_6$alkoxy, or $C_1$-$C_6$haloalkoxy;

$R_7$, $R_{13}$, $R_{14}$, $R_{15}$, $R_{16}$, $R_{17}$ and $R_{18}$ independently of one another are $C_1$-$C_6$alkyl, $C_1$-$C_6$haloalkyl, $C_1$-$C_6$cycloalkyl or $C_1$-$C_6$halocycloalkyl; or $C_1$-$C_6$alkyl, $C_1$-$C_6$haloalkyl, $C_1$-$C_6$cycloalkyl or $C_1$-$C_6$halocycloalkyl substituted by $C_1$-$C_6$alkyl, $C_1$-$C_6$haloalkyl, $C_1$-$C_6$cycloalkyl, $C_1$-$C_6$halocycloalkyl, $C_1$-$C_6$alkoxy or $C_1$-$C_6$haloalkoxy; and agronomically acceptable salts/isomers/enantiomers/tautomers of those compounds.

Compounds I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Where appropriate, the corresponding internal salts can furthermore be formed. Preferred within the scope of the invention are agrochemically advantageous salts; however, the invention also encompasses salts which have disadvantage for agrochemical use, for example salts which are toxic to bees or fish, and which are employed, for example, for the isolation or purification of free compounds I or agrochemically utilizable salts thereof. Owing to the close relationship between the compounds I in free form and in the form of their salts, for the purposes of the invention the free compounds I or their salts hereinabove and hereinbelow are respectively to be understood as including, where appropriate, the corresponding salts or the free compounds I. The same applies analogously to tautomers of compounds I and salts thereof. In general, the free form is preferred in each case.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, heptyl and octyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_3$-$C_8$alkenyl groups which are mono-, di- or trisubstituted by halogen, preference is given to those having a chain length of from 3 to 5 carbon atoms.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl. Among the alkynyl groups which are mono- or polysubstituted by halogen, preference is given to those having a chain length of from 3 to 5 carbon atoms.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl. Alkoxyalkoxy groups preferably have a chain length of from 1 to 8 carbon atoms. Examples of alkoxyalkoxy groups are: methoxymethoxy, methoxyethoxy, methoxypropoxy, ethoxymethoxy, ethoxyethoxy, propoxymethoxy or butoxybutoxy. Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms. Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

$R_2$ together with $R_3$ may form a $C_2$-$C_6$alkylene or $C_3$-$C_6$alkenylene bridge which may be interrupted by nitrogene, oxygen and/or —C(O)—, or by —S(O)$_m$— and, together with the phenyl ring they substitute, may form a bicyclic ring system such as, for example, naphthalene, tetrahydronaphthalene, indene, indane, quinoline, isoquinoline, quinoxaline, cinnoline, quinazoline, chroman, isochroman, indole, isoindole, indoline, isoindoline, benzodioxane, benzofuran, dihydrobenzofuran, benzothiophene, dihydrobenzothiophene, benzoxazole, benzimidazole or indazole.

According to the present invention, a three- to ten-membered, monocyclic or fused bicyclic ring system which may be aromatic, partially saturated or fully saturated is, for example, selected from the group consisting of cyclopropyl, cyclobutyl, cyclopentyl, cyclohexyl, where said cycloalkyl groups for their part may be preferably unsubstituted or substituted by $C_1$-$C_6$alkyl or halogen, or is phenyl, naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

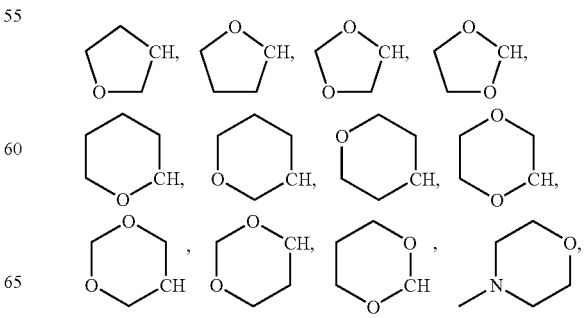

-continued

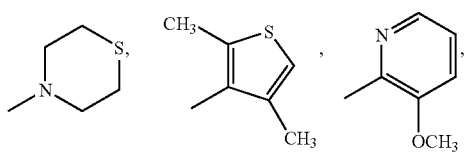

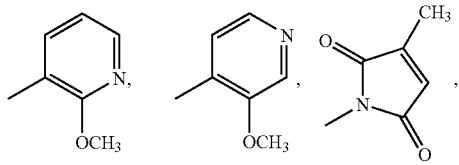

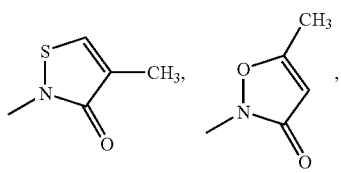

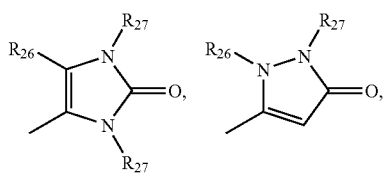

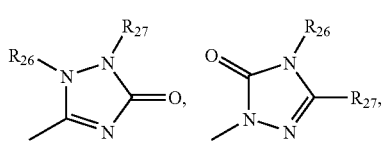

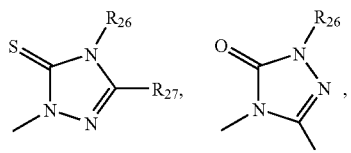

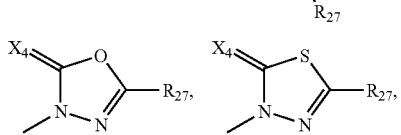

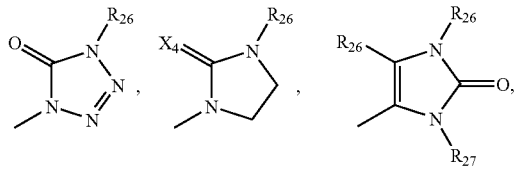

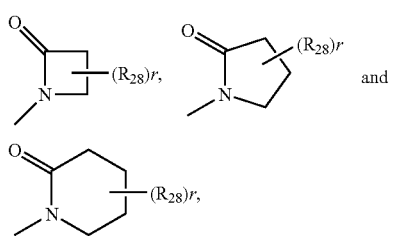

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r=1, 2, 3 or 4.

Where no free valency is indicated in those definitions, for example as in

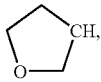

the linkage site is located at the carbon atom labelled "CH" or in a case such as, for example,

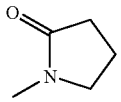

at the bonding site indicated at the bottom left.

$Y_1$ as $C_3$-$C_6$cycloalkylene, which may be mono-, di- or trisubstituted by $R_{10}$, represents together with the adjacent nitrogen and sulfur atoms for example the following groups:

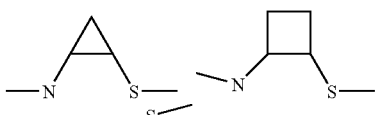

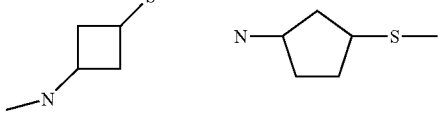

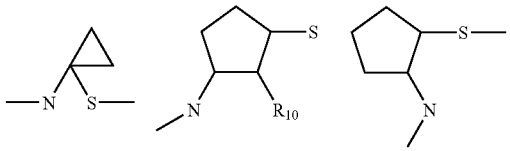

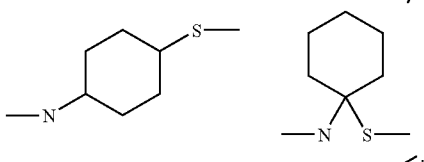

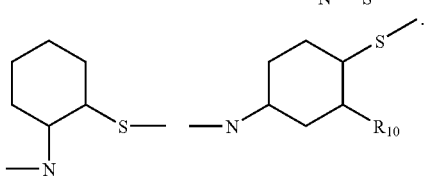

Preference is given to compounds of formula I wherein
a) $R_5$ is hydrogen, halogen, $C_1$-$C_6$alkyl or halo-$C_1$-$C_6$alkyl, preferably hydrogen; and/or
b) $R_4$ is hydrogen halogen, $C_1$-$C_6$alkyl or halo-$C_1$-$C_6$alkyl, preferably hydrogen; and/or
c) $S_2$ is hydrogen, halogen or $C_1$-$C_8$alkyl, preferably hydrogen.

Special mention should be made of compounds of formula I wherein $S_1$ is hydrogen, halogen, $C_1$-$C_6$alkyl or halo-$C_1$-$C_6$alkyl, preferably halogen or $C_1$-$C_6$alkyl, most preferably, methyl or chlorine.

An outstanding group of compounds of formula I comprises those compounds wherein $S_3$ is hydrogen, $C_1$-$C_6$haloalkyl, $C_1$-$C_6$haloalkoxy, halogen-substituted phenyl, halogen-substituted phenoxy, preferably $C_1$-$C_6$-fluoroalkyl, most preferably trifluoromethyl, —CF(CF₃)₂, —CF₂CF₃ or CH(CF₃)₂, halo-$C_1$-$C_6$alkoxy, preferably fluoro-$C_1$-$C_6$alkoxy, most preferably trifluoromethoxy.

In preferred compound of formula I, $R_1$ is halogen or $C_1$-$C_4$alkyl, preferably methyl, iodine, bromine or chlorine.

Further compounds of formula I are preferred wherein n is 1.

$R_2$ and $R_3$ independently are preferably hydrogen, halogen, $C_1$-$C_6$alkyl or $C_1$-$C_6$halo-alkyl, preferably hydrogen.

Special emphasis should also be given to compounds of formula I wherein a) $Y_1$ is $C_1$-$C_6$alkylene or $C_1$-$C_6$cyclo-alkylene substituted with $C_1$-$C_6$alkyl, preferably C(CH₃)₂CH₂, C(CH₃)₂(CH₂)₂, C(CH₃)₂(CH₂)₃, C(CH₃)₂(CH₂)₄ or CH(CH₃); and/or b) $Y_2$ is $C_1$-$C_6$alkylene, $C_1$-$C_6$cyclo-alkylene, preferably methylene;

c) $Y_3$ is hydrogen or $C_1$-$C_6$alkyl, preferably hydrogen;

d) Z is hydrogen, —C(O)$R_6$, —C(O)O—$R_7$, —CONR₁₃R₁₄, —SO₂R₁₅ or —OP(OR₁₆)(OR₁₇)—OR₁₈; wherein $R_6$ is $C_1$-$C_6$alkyl, $C_1$-$C_6$haloalkyl, $C_1$-$C_6$cycloalkyl or $C_1$-$C_6$halocycloalkyl.

$R_7$, $R_{13}$, $R_{14}$, $R_{15}$, $R_{16}$, $R_{17}$ and $R_{18}$ independently of one another are $C_1$-$C_6$alkyl or $C_1$-$C_6$haloalkyl; or $C_1$-$C_6$alkyl or $C_1$-$C_6$haloalkyl substituted with $C_1$-$C_6$alkyl or $C_1$-$C_6$haloalkyl;

Preferably Z is hydrogen, —C(O)$R_6$, —C(O)O—$R_7$, —CONR₁₃R₁₄, —SO₂R₁₅ or —OP(OR₁₆)(OR₁₇)—OR₁₈; wherein $R_6$ is $C_1$-$C_6$alkyl or $C_1$-$C_6$haloalkyl; wherein $R_7$, $R_{13}$, $R_{14}$, $R_{15}$, $R_{16}$, $R_{17}$ and $R_{18}$ independently of one another are methyl, ethyl, butyl or tert-butyl.

The process according to the invention for preparing compounds of the formula I is carried out analogously to known processes, for example those described in US 2004/0097595A1 and EP-A-1006107.

Compounds of formula I, wherein $R_4$ is hydrogen, can be prepared, for example, by reacting a compound of formula II

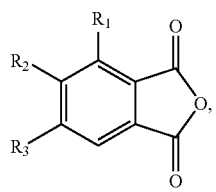

(II)

wherein $R_1$, $R_2$ and $R_3$ are defined as in formula I, with a compound of formula III

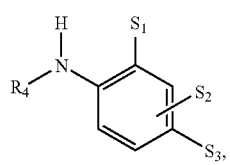

(III)

wherein $S_1$, $S_2$ and $S_3$ are defined as in formula I and $R_4$ is hydrogen, in the presence of inert solvents and if appropriate, in the presence of a base, to a compound of formula IV

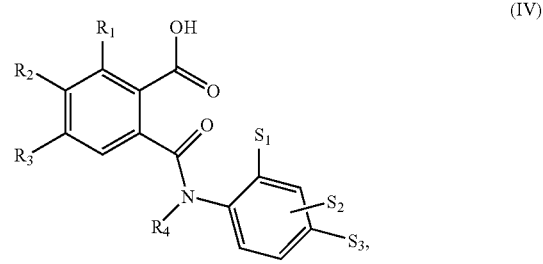

(IV)

wherein $R_1$, $R_2$, $R_3$, $S_1$, $S_2$ and $S_3$ are defined as in formula I and $R_4$ is hydrogen, which is converted with a condensing agent to a compound of formula V

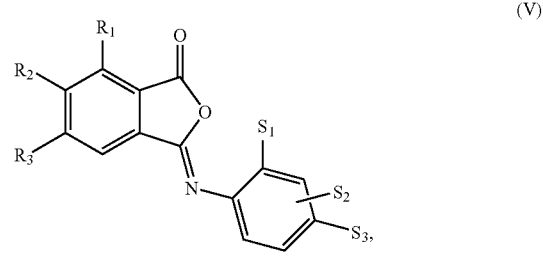

(V)

wherein $R_1$, $R_2$, $R_3$, $S_1$, $S_2$ and $S_3$ are defined as in formula I, which is reacted in the presence of an inert solvent with a compound of formula VI

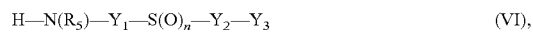

H—N($R_5$)—$Y_1$—S(O)$_n$—$Y_2$—$Y_3$ (VI), wherein n, $R_5$, $Y_1$, $Y_2$ and $Y_3$ are as defined in formula I, to a compound of formula VII

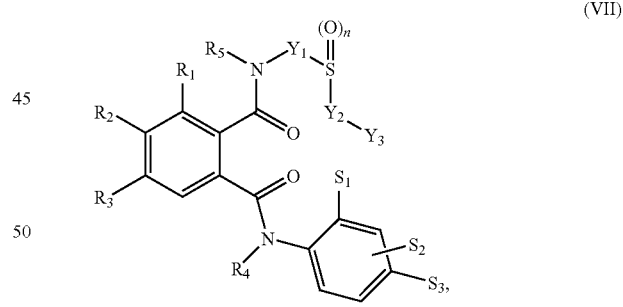

(VII)

wherein n, $R_1$, $R_2$, $R_3$, $R_5$, $S_1$, $S_2$, $S_3$, $Y_1$, $Y_2$ and $Y_3$ are defined as in formula I and $R_4$ is hydrogen. Compounds of formula VII, wherein $R_4$ is different from hydrogen, can be prepared by condensation of a compound of formula IV, wherein $R_4$ is different from hydrogen with a compound of formula VI in the presence of an inert solvent. Analogous reactions are described, e.g. on pages 9 to 17 of EP-A-1006107.

The compounds of formula I may be made from a corresponding compound of formula VII according to known procedures (n=0: step A and B, n=1: step B, see e.g. M. Reggelin, C. Zur, Synthesis, 2000, 1). An alternative pathway is the preparation of a sulfilimine of formula I (n=0) from a sulfide of formula VII (n=0) (step B). Oxidation of a compound of formula I (n=0) gives a sulfoximine of formula I (n=1, step A).

Classical oxidation reagents (step A: sulfide-sulfoxide or sulfilimine-sulfoximine) are $KMnO_4$, mCPBA, $NaIO_4/RuO_2$, $H_2O_2$, oxone. For the transformation sulfoxide-sulfoximine or sulfide sulfilimine (step B), typical reagents are $NaN_3/H_2SO_4$, O-mesitylenesulfonylhydroxylamine (MSH), or metal-catalyzed methods such as $RN_3/FeCl_2$, PhI=N—R/CuOTf, PhI=N—R/Cu(OTf)$_2$, PhI=N—R/CuPF$_6$, PHI(OAc)$_2$/R—NH$_2$/MgO/Ru$_2$(OAc)$_4$ or oxaziridines (e.g. 3-(4-cyano-phenyl)-oxaziridine-2-carboxylic acid tert-butyl ester).

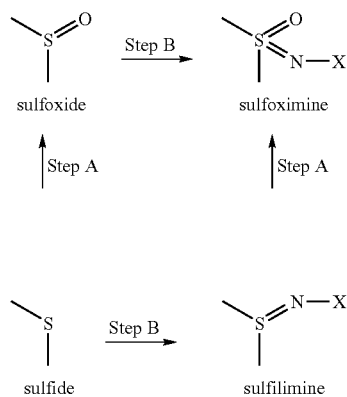

Alternatively, compounds of formula I can be prepared by reacting a compound of formula V, wherein $R_1$, $R_2$, $R_3$, $S_1$, $S_2$ and $S_3$ are defined as in formula I, with a compound of formula VIa

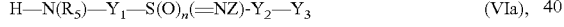 (VIa), wherein n, $R_5$, $Y_1$, $Y_2$, $Y_3$ and Z are as defined in formula I, in the presence of an inert solvent. Compounds of formula VIa can be prepared according to literature methods (H. Okamura, C. Bolm, Chemistry Letters (2004), 33(5), 482-487).

Compounds of formula I, wherein $R_5$ is hydrogen, can also be prepared according to EP-A-1006107 by reacting a phthalic anhydride derivative of formula II

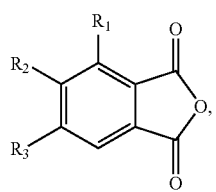

wherein $R_1$, $R_2$ and $R_3$ are defined as in formula I, in the presence of an inert solvent with a compound of formula VI

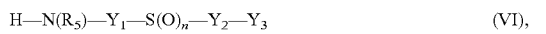 (VI), wherein n, $Y_1$, $Y_2$ and $Y_3$ are as defined in formula I, $R_5$ is hydrogen, to a compound of formula VIII

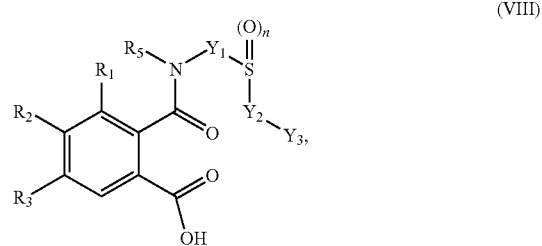

wherein n, $R_1$, $R_2R_3$, $Y_1$, $Y_2$ and $Y_3$ are defined as in formula I and $R_5$ is hydrogen, which is converted with a condensing agent to a compound of formula IX

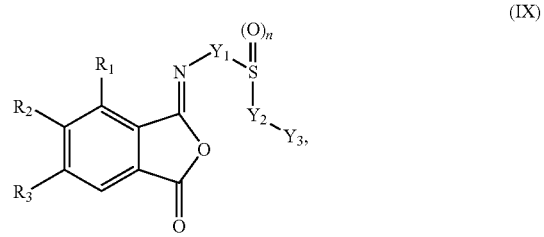

wherein n, $R_1$, $R_2$, $R_3$, $Y_1$, $Y_2$ and $Y_3$ are defined as in formula I, which is reacted with a compound of formula IIIa

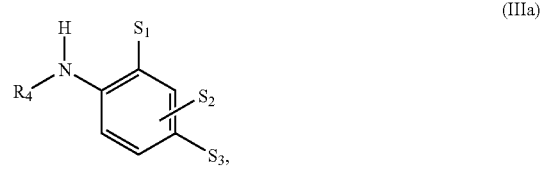

wherein $R_4$, $S_1$, $S_2$ and $S_3$ are defined as in formula I, in the presence of inert solvents to a compound of formula VII. Compounds of formula VII, wherein $R_5$ is different from hydrogen, can be prepared by condensation of a compound of formula VIII, wherein $R_5$ is different from hydrogen with a compound of formula VI in the presence of an inert solvent. Compounds of formula VII can be converted to compounds of formula I as mentioned above.

Alternatively, compounds of formula I can be prepared by reacting a compound of formula IIIa, wherein $R_4$, $S_1$, $S_2$ and $S_3$ are as defined in formula I, with a compound of formula IXa

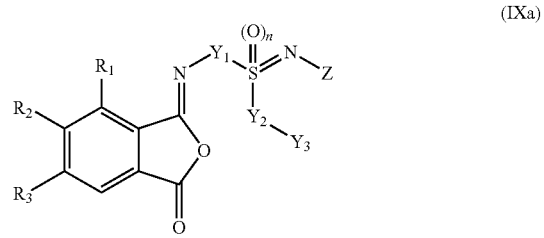

wherein Z, n, $R_1$, $R_2$, $R_3$, $Y_1$, $Y_2$ and $Y_3$ are defined as in formula I, which can be made from a compound of formula VIIIa

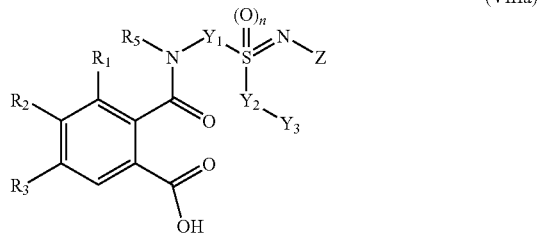

wherein Z, n, $R_1$, $R_2$, $R_3$, $Y_1$, $Y_2$ and $Y_3$ are defined as in formula I and $R_5$ is hydrogen, which can be made by reacting a compound of formula II with a compound of formula VIa wherein n, $Y_1$, $Y_2$ and $Y_3$ are defined as in formula I and $R_5$ is hydrogen.

The reactions described hereinabove and hereinbelow are carried out in a manner known per se, for example in the absence or, normally, in the presence of a suitable solvent or diluent or of a mixture of these, the process being carried out, as required, with cooling, at room temperature or with heating, for example in a temperature range of from approximately −80° C. to the boiling point of the reaction mixture, preferably from approximately −20° C. to approximately +150° C., and, if required, in a sealed vessel, under reduced, normal or elevated pressure, in an inert gas atmosphere and/or under anhydrous conditions. Especially advantageous reaction conditions can be seen from the examples.

Examples of such solvents or diluents which may be mentioned are: aromatic, aliphatic and alicyclic hydrocarbons and halohydrocarbons such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters such as ethyl acetate; ethers such as diethyl ether, dipropyl ether, diisopropyl ether, dibutyl ether, tert-butyl methyl ether, ethyleneglycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides such as N,N-dimethylformamide, N,N-diethylformamide, N,N-dimethylacetamide, N-methylpyrrolidone or hexamethylphosphoric triamide; nitriles, such as acetonitrile or propionitrile; and sulfoxides, such as dimethyl sulfoxide.

Unless otherwise specified, the starting materials mentioned hereinabove and hereinbelow, which are used for the preparation of the compounds I or, where appropriate, the tautomers thereof, in each case in free form or in salt form, are known or can be prepared by methods known per se, for example in accordance with the information given below.

A compound I can be converted in a manner known per se into another compound I by replacing one or more substituents of the starting compound I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;
from the order Diptera, for example,
*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;
from the order Heteroptera, for example,

*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;
from the order Homoptera, for example,
*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*;
from the order Hymenoptera, for example,
*Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;
from the order Isoptera, for example,
*Reticulitermes* spp.;
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;
from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Periplaneta* spp. and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis*;
from the order Thysanoptera, for example,
*Frankliniella* spp., *Hercinothrips* spp., *Scirtothrips aurantii, Taeniothrips* spp., *Thrips palmi* and *Thrips tabaci*; and
from the order Thysanura, for example,
*Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA(c), CryIF, CryIF(a2), CryIIA(b), CryIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIA toxin); Nature-Gard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain *Coleoptera* insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NU00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

Other indication areas for the active ingredients of the invention are the protection of stored products and stores and of material and, in the hygiene sector, especially the protection of domestic animals and livestock against pests of said type.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorptive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quaternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates.

Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (un-substituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:
active ingredient: 1 to 95%, preferably 5 to 20%
surfactant: 1 to 30%, preferably 10 to 20%
solvent: 5 to 98%, preferably 70 to 85%

Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

The activity of the compositions according to the invention can be broadened considerably, and adapted to prevailing circumstances, by adding other insecticidally or acaricidally active ingredients. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and Bacillus thuringiensis preparations.

Examples of especially suitable mixing partners for the compounds of formula I include the following compounds selected from the group M:

Group M:
an adjuvant selected from the group of substances consisting of petroleum oils (alternative name) (628),
an acaricide selected from the group of substances consisting of 1,1-bis(4-chlorophenyl)-2-ethoxyethanol (IUPAC name) (910), 2,4-dichlorophenyl benzenesulfonate (IUPAC/Chemical Abstracts name) (1059), 2-fluoro-N-methyl-N-1-naphthylacetamide (IUPAC name) (1295), 4-chlorophenyl phenyl sulfone (IUPAC name) (981), abamectin (1), acequinocyl (3), acetoprole [CCN], acrinathrin (9), aldicarb (16), aldoxycarb (863), alphacypermethrin (202), amidithion (870), amidoflumet [CCN], amidothioate (872), amiton (875), amiton hydrogen oxalate (875), amitraz (24), aramite (881), arsenous oxide (882), AVI 382 (compound code), AZ 60541 (compound code), azinphos-ethyl (44), azinphos-methyl (45), azobenzene (IUPAC name) (888), azocyclotin (46), azothoate (889), benomyl (62), benoxafos (alternative name) [CCN], benzoximate (71), benzyl benzoate (IUPAC name) [CCN], bifenazate (74), bifenthrin (76), binapacryl (907), brofenvalerate (alternative name), bromocyclen (918), bromophos (920), bromophos-ethyl (921), bromopropylate (94), buprofezin (99), butocarboxim (103), butoxycarboxim (104), butylpyridaben (alternative name), calcium polysulfide (IUPAC name) (111), camphechlor (941), carbanolate (943), carbaryl (115), carbofuran (118), carbophenothion (947), CGA 50'439 (development code) (125), chinomethionat (126), chlorbenside (959), chlordimeform (964), chlordimeform hydrochloride (964), chlorfenapyr (130), chlorfenethol (968), chlorfenson (970), chlorfensulphide (971), chlorfenvinphos (131), chlorobenzilate (975), chloromebuform (977), chloromethiuron (978), chloropropylate (983), chlorpyrifos (145), chlorpyrifos-methyl (146), chlorthiophos (994), cinerin I (696), cinerin II (696), cinerins (696), clofentezine (158), closantel (alternative name) [CCN], coumaphos (174), crotamiton (alternative name) [CCN], crotoxyphos (1010), cufraneb (1013), cyanthoate (1020), cyflumetofen (CAS Reg. No.: 400882-07-7), cyhalothrin (196), cyhexatin (199), cypermethrin (201), DCPM (1032), DDT (219), demephion (1037), demephion-O (1037), demephion-S (1037), demeton (1038), demeton-methyl (224), demeton-O (1038), demeton-O-methyl (224), demeton-S (1038), demeton-S-methyl (224), demeton-S-methylsulphon (1039), diafenthiuron (226), dialifos (1042), diazinon (227), dichlofluanid (230), dichlorvos (236), dicliphos (alternative name), dicofol (242), dicrotophos (243), dienochlor (1071), dimefox (1081), dimethoate (262), dinactin (alternative name) (653), dinex (1089), dinex-diclexine (1089), dinobuton (269), dinocap (270), dinocap-4 [CCN], dinocap-6 [CCN], dinocton (1090), dinopenton (1092), dinosulfon (1097), dinoterbon (1098), dioxathion (1102), diphenyl sulfone (IUPAC name) (1103), disulfuram (alternative name) [CCN], disulfoton (278), DNOC (282), dofenapyn (1113), doramectin (alternative name) [CCN], endosulfan (294), endothion (1121), EPN (297), eprinomectin (alternative name) [CCN], ethion (309), ethoate-methyl (1134), etoxazole (320), etrimfos (1142), fenazaflor (1147), fenazaquin (328), fenbutatin oxide (330), fenothiocarb (337), fenpropathrin (342), fenpyrad (alternative name), fenpyroximate (345), fenson (1157), fentrifanil (1161), fenvalerate (349), fipronil (354), fluacrypyrim (360), fluazuron (1166), flubenzimine (1167), flucycloxuron (366), flucythrinate (367), fluenetil (1169), flufenoxuron (370), flumethrin (372), fluorbenside (1174), fluvalinate (1184), FMC 1137 (development code) (1185), formetanate (405), formetanate hydrochloride (405), formothion (1192), formparanate (1193), gamma-HCH (430), glyodin (1205), halfenprox (424), heptenophos (432), hexadecyl cyclopropanecarboxylate (IUPAC/Chemical Abstracts name) (1216), hexythiazox (441), iodomethane (IUPAC name) (542), isocarbophos (alternative name) (473), isopropyl O-(methoxyaminothiophosphoryl)salicylate (IUPAC name) (473), ivermectin (alternative name) [CCN], jasmolin I (696), jasmolin II (696), jodfenphos (1248), lindane (430), lufenuron (490), malathion (492), malonoben (1254), mecarbam (502), mephosfolan (1261), mesulfen (alternative name) [CCN], methacrifos (1266), methamidophos (527), methidathion (529), methiocarb (530), methomyl (531), methyl bromide (537), metolcarb (550), mevinphos (556), mexacarbate (1290), milbemectin (557), milbemycin oxime (alternative name) [CCN], mipafox (1293), monocrotophos (561), morphothion (1300), moxidectin (alternative name) [CCN], naled (567), NC-184 (compound code), NC-512 (compound code), nifluridide (1309), nikkomycins (alternative name) [CCN], nitrilacarb (1313), nitrilacarb 1:1 zinc chloride complex (1313), NNI-0101 (compound code), NNI-0250 (compound code), omethoate (594), oxamyl (602), oxydeprofos (1324), oxydisulfoton (1325), pp'-DDT (219), parathion (615), permethrin (626), petroleum oils (alternative name) (628), phenkapton (1330), phenthoate (631), phorate (636), phosalone (637), phosfolan (1338), phosmet (638), phosphamidon (639), phoxim (642), pirimiphos-methyl (652), polychloroterpenes (traditional name) (1347), polynactins (alternative name) (653), proclonol (1350), profenofos (662), promacyl (1354), propargite (671), propetamphos (673), propoxur (678), prothidathion (1360), prothoate (1362), pyrethrin I (696), pyrethrin II (696), pyrethrins (696), pyridaben (699), pyridaphenthion (701), pyrimidifen (706), pyrimitate (1370), quinalphos (711), quintiofos (1381), R-1492 (development code) (1382), RA-17 (development code) (1383), rotenone (722), schradan (1389), sebufos (alternative name), selamectin (alternative name) [CCN], SI-0009 (compound code), sophamide (1402), spirodiclofen (738), spiromesifen (739), SSI-121 (development code) (1404), sulfuram (alternative name) [CCN], sulfluramid (750), sulfotep (753), sulfur (754), SZI-121 (development code) (757), tau-fluvalinate (398), tebufenpyrad (763), TEPP (1417), terbam (alternative name), tetrachlorvinphos (777), tetradifon (786), tetranactin (alternative name) (653), tetrasul (1425), thiafenox (alternative name), thiocarboxime (1431), thiofanox (800), thiometon (801), thioquinox (1436), thuringiensin (alternative name) [CCN], triamiphos (1441), triarathene (1443), triazophos (820), triazuron (alternative name), trichlorfon (824), trifenofos (1455), trinactin (alternative name) (653), vamidothion (847), vaniliprole [CCN] and YI-5302 (compound code), an algicide selected from the group of substances consisting of bethoxazin [CCN], copper dioctanoate (IUPAC name) (170), copper sulfate (172), cybutryne [CCN], dichlone (1052), dichlorophen (232), endothal (295), fentin (347), hydrated lime [CCN], nabam (566), quinoclamine (714), quinonamid (1379), simazine (730), triphenyltin acetate (IUPAC name) (347) and triphenyltin hydroxide (IUPAC name) (347), an anthelmintic selected from the group of substances consisting of abamectin (1), crufomate (1011), doramectin (alternative name) [CCN], emamectin (291), emamectin benzoate (291), eprinomectin (alternative name) [CCN], ivermectin (alternative name) [CCN], milbemycin oxime (alternative name) [CCN], moxidectin (alternative name) [CCN], piperazine [CCN], selamectin (alternative name) [CCN], spinosad (737) and thiophanate (1435), an avicide selected from the group of substances consisting of chloralose (127), endrin (1122), fenthion (346), pyridin-4-amine (IUPAC name) (23) and strychnine (745), a bactericide selected from the group of substances consisting of 1-hydroxy-1H-pyridine-2-thione (IUPAC name) (1222), 4-(quinoxalin-2-ylamino)benzenesulfonamide (IUPAC name) (748), 8-hydroxyquinoline sulfate (446), bronopol (97), copper dioctanoate (IUPAC name) (170), copper hydroxide (IUPAC name) (169), cresol [CCN], dichlorophen (232), dipyrithione (1105), dodicin (1112), fenaminosulf (1144), formaldehyde (404), hydrargaphen (alternative name) [CCN], kasugamycin (483), kasugamycin hydrochloride hydrate (483), nickel bis(dimethyldithiocarbamate) (IUPAC name) (1308), nitrapyrin (580), octhilinone (590), oxolinic acid (606), oxytetracycline (611), potassium hydroxyquinoline sulfate (446), probenazole (658), streptomycin (744), streptomycin sesquisulfate (744), tecloftalam (766) and thiomersal (alternative name) [CCN], a biological agent selected from the group of substances consisting of *Adoxophyes orana* GV (alternative name) (12), *Agrobacterium radiobacter* (alternative name) (13), *Amblyseius* spp. (alternative name) (19), *Anagrapha falcifera* NPV (alternative name) (28), *Anagrus atomus* (alternative name) (29), *Aphelinus abdominalis* (alternative name) (33), *Aphidius colemani* (alternative name) (34), *Aphidoletes aphidimyza* (alternative name) (35), *Autographa californica* NPV (alternative name) (38), *Bacillus firmus* (alternative name) (48), *Bacillus sphaericus* Neide (scientific name) (49), *Bacillus thuringiensis* Berliner (scientific name) (51), *Bacillus thur-*

*ingiensis* subsp. *aizawai* (scientific name) (51), *Bacillus thuringiensis* subsp. *israelensis* (scientific name) (51), *Bacillus thuringiensis* subsp. *japonensis* (scientific name) (51), *Bacillus thuringiensis* subsp. *kurstaki* (scientific name) (51), *Bacillus thuringiensis* subsp. *tenebrionis* (scientific name) (51), *Beauveria bassiana* (alternative name) (53), *Beauveria brongniartii* (alternative name) (54), *Chrysoperla carnea* (alternative name) (151), *Cryptolaemus montrouzieri* (alternative name) (178), *Cydia pomonella* GV (alternative name) (191), *Dacnusa sibirica* (alternative name) (212), *Diglyphus isaea* (alternative name) (254), *Encarsia formosa* (scientific name) (293), *Eretmocerus eremicus* (alternative name) (300), *Helicoverpa zea* NPV (alternative name) (431), *Heterorhabditis bacteriophora* and *H. megidis* (alternative name) (433), *Hippodamia convergens* (alternative name) (442), *Leptomastix dactylopil* (alternative name) (488), *Macrolophus caliginosus* (alternative name) (491), *Mamestra brassicae* NPV (alternative name) (494), *Metaphycus helvolus* (alternative name) (522), *Metarhizium anisopliae* var. *acridum* (scientific name) (523), *Metarhizium anisopliae* var. *anisopliae* (scientific name) (523), *Neodiprion sertifer* NPV and *N. lecontei* NPV (alternative name) (575), *Orius* spp. (alternative name) (596), *Paecilomyces fumosoroseus* (alternative name) (613), *Phytoseiulus persimilis* (alternative name) (644), *Spodoptera exigua* multicapsid nuclear polyhedrosis virus (scientific name) (741), *Steinernema bibionis* (alternative name) (742), *Steinernema carpocapsae* (alternative name) (742), *Steinernema feltiae* (alternative name) (742), *Steinernema* glaseri (alternative name) (742), *Steinemema riobrave* (alternative name) (742), *Steinernema riobravis* (alternative name) (742), *Steinernema scapterisci* (alternative name) (742), *Steinernema* spp. (alternative name) (742), *Trichogramma* spp. (alternative name) (826), *Typhlodromus occidentalis* (alternative name) (844) and *Verticillium lecanii* (alternative name) (848), a soil sterilant selected from the group of substances consisting of iodomethane (IUPAC name) (542) and methyl bromide (537), a chemosterilant selected from the group of substances consisting of apholate [CCN], bisazir (alternative name) [CCN], busulfan (alternative name) [CCN], diflubenzuron (250), dimatif (alternative name) [CCN], hemel [CCN], hempa [CCN], metepa [CCN], methiotepa [CCN], methyl apholate [CCN], morzid [CCN], penfluoron (alternative name) [CCN], tepa [CCN], thiohempa (alternative name) [CCN], thiotepa (alternative name) [CCN], tretamine (alternative name) [CCN] and uredepa (alternative name) [CCN], an insect pheromone selected from the group of substances consisting of (E)-dec-5-en-1-yl acetate with (E)-dec-5-en-1-ol (IUPAC name) (222), (E)-tridec-4-en-1-yl acetate (IUPAC name) (829), (E)-6-methylhept-2-en-4-ol (IUPAC name) (541), (E,Z)-tetradeca-4,10-dien-1-yl acetate (IUPAC name) (779), (Z)-dodec-7-en-1-yl acetate (IUPAC name) (285), (Z)-hexadec-11-enal (IUPAC name) (436), (Z)-hexadec-11-en-1-yl acetate (IUPAC name) (437), (Z)-hexadec-13-en-11-yn-1-yl acetate (IUPAC name) (438), (Z)-icos-13-en-10-one (IUPAC name) (448), (Z)-tetradec-7-en-1-al (IUPAC name) (782), (Z)-tetradec-9-en-1-ol (IUPAC name) (783), (Z)-tetradec-9-en-1-yl acetate (IUPAC name) (784), (7E,9Z)-dodeca-7,9-dien-1-yl acetate (IUPAC name) (283), (9Z,11E)-tetradeca-9,11-dien-1-yl acetate (IUPAC name) (780), (9Z,12E)-tetradeca-9,12-dien-1-yl acetate (IUPAC name) (781), 14-methyloctadec-1-ene (IUPAC name) (545), 4-methylnonan-5-ol with 4-methylnonan-5-one (IUPAC name) (544), alpha-multistriatin (alternative name) [CCN], brevicomin (alternative name) [CCN], codlelure (alternative name) [CCN], codlemone (alternative name) (167), cuelure (alternative name) (179), disparlure (277), dodec-8-en-1-yl acetate (IUPAC name) (286), dodec-9-en-1-yl acetate (IUPAC name) (287), dodeca-8,10-dien-1-yl acetate (IUPAC name) (284), dominicalure (alternative name) [CCN], ethyl 4-methyloctanoate (IUPAC name) (317), eugenol (alternative name) [CCN], frontalin (alternative name) [CCN], gossyplure (alternative name) (420), grandlure (421), grandlure I (alternative name) (421), grandlure II (alternative name) (421), grandlure III (alternative name) (421), grandlure IV (alternative name) (421), hexylure [CCN], ipsdienol (alternative name) [CCN], ipsenol (alternative name) [CCN], japonilure (alternative name) (481), lineatin (alternative name) [CCN], litlure (alternative name) [CCN], looplure (alternative name) [CCN], medlure [CCN], megatomoic acid (alternative name) [CCN], methyl eugenol (alternative name) (540), muscalure (563), octadeca-2,13-dien-1-yl acetate (IUPAC name) (588), octadeca-3,13-dien-1-yl acetate (IUPAC name) (589), orfralure (alternative name) [CCN], oryctalure (alternative name) (317), ostramone (alternative name) [CCN], siglure [CCN], sordidin (alternative name) (736), sulcatol (alternative name) [CCN], tetradec-11-en-1-yl acetate (IUPAC name) (785), trimedlure (839), trimedlure A (alternative name) (839), trimedlure $B_1$ (alternative name) (839), trimedlure $B_2$ (alternative name) (839), trimedlure C (alternative name) (839) and trunc-call (alternative name) [CCN], an insect repellent selected from the group of substances consisting of 2-(octylthio)-ethanol (IUPAC name) (591), butopyronoxyl (933), butoxy(polypropylene glycol) (936), dibutyl adipate (IUPAC name) (1046), dibutyl phthalate (1047), dibutyl succinate (IUPAC name) (1048), diethyltoluamide [CCN], dimethyl carbate [CCN], dimethyl phthalate [CCN], ethyl hexanediol (1137), hexamide [CCN], methoquin-butyl (1276), methylneodecanamide [CCN], oxamate [CCN] and picaridin [CCN], an insecticide selected from the group of substances consisting of 1,1-dichloro-1-nitroethane (IUPAC/Chemical Abstracts name) (1058), 1,1-dichloro-2,2-bis(4-ethylphenyl)-ethane (IUPAC name) (1056), 1,2-dichloropropane (IUPAC/Chemical Abstracts name) (1062), 1,2-dichloropropane with 1,3-dichloropropene (IUPAC name) (1063), 1-bromo-2-chloroethane (IUPAC/Chemical Abstracts name) (916), 2,2,2-trichloro-1-(3,4-dichlorophenyl)ethyl acetate (IUPAC name) (1451), 2,2-dichlorovinyl 2-ethylsulfinylethyl methyl phosphate (IUPAC name) (1066), 2-(1,3-dithiolan-2-yl)phenyl dimethylcarbamate (IUPAC/Chemical Abstracts name) (1109), 2-(2-butoxyethoxy)ethyl thiocyanate (IUPAC/Chemical Abstracts name) (935), 2-(4,5-dimethyl-1,3-dioxolan-2-yl)phenyl methylcarbamate (IUPAC/Chemical Abstracts name) (1084), 2-(4-chloro-3,5-xylyloxy)ethanol (IUPAC name) (986), 2-chlorovinyl diethyl phosphate (IUPAC name) (984), 2-imidazolidone (IUPAC name) (1225), 2-isovalerylindan-1,3-dione (IUPAC name) (1246), 2-methyl(prop-2-ynyl)aminophenyl methylcarbamate (IUPAC name) (1284), 2-thiocyanatoethyl laurate (IUPAC name) (1433), 3-bromo-1-chloroprop-1-ene (IUPAC name) (917), 3-methyl-1-phenylpyrazol-5-yl dimethylcarbamate (IUPAC name) (1283), 4-methyl(prop-2-ynyl)amino-3,5-xylyl methylcarbamate (IUPAC name) (1285), 5,5-dimethyl-3-oxocyclohex-1-enyl dimethylcarbamate (IUPAC name) (1085), abamectin (1), acephate (2), acetamiprid (4), acethion (alternative name) [CCN], acetoprole [CCN], acrinathrin (9), acrylonitrile (IUPAC name) (861), alanycarb (15), aldicarb (16), aldoxycarb (863), aldrin (864), allethrin (17), allosamidin (alternative name) [CCN], allyxycarb (866), alpha-cypermethrin (202), alpha-ecdysone (alternative name) [CCN], aluminium phosphide (640), amidithion (870), amidothioate (872), aminocarb (873), amiton (875), amiton hydrogen oxalate (875), amitraz (24), anabasine (877), athidathion (883), AVI 382 (compound code), AZ 60541 (compound code), azadirachtin (alternative name) (41), azamethiphos (42), azinphos-ethyl (44), azinphos-methyl (45), azothoate (889), *Bacillus thuringiensis* delta endotoxins (alternative name) (52), barium hexafluorosilicate (alternative name) [CCN], barium polysulfide (IUPAC/Chemical Abstracts name) (892), barthrin [CCN], Bayer 22/190 (development code) (893), Bayer 22408 (development code) (894), bendiocarb (58), benfuracarb (60), bensultap (66), beta-cyfluthrin (194), beta-cypermethrin (203), bifenthrin (76), bioallethrin (78), bioallethrin S-cyclopentenyl isomer (alternative name) (79), bioethanomethrin [CCN], biopermethrin (908), bioresmethrin (80), bis(2-chloroethyl)ether (IUPAC name) (909), bistrifluoron (83), borax (86), brofenvalerate (alternative name), bromfenvinfos (914), bromocyclen (918), bromo-DDT (alternative name) [CCN], bromophos (920), bromophos-ethyl (921), bufencarb (924), buprofezin (99), butacarb (926), butathiofos (927), butocarboxim (103), butonate (932), butoxycarboxim (104), butylpyridaben (alternative name), cadusafos (109), calcium arsenate [CCN], calcium cyanide (444), calcium polysulfide (IUPAC name) (111), camphechlor (941), carbanolate (943), carbaryl (115), carbofuran (118), carbon disulfide (IUPAC/Chemical Abstracts name) (945), carbon tetrachloride (IUPAC name) (946), carbophenothion (947), carbosulfan (119), cartap (123), cartap hydrochloride (123), cevadine (alternative name) (725), chlorbicyclen (960), chlordane (128), chlordecone (963), chlordimeform (964), chlordimeform hydrochloride (964), chlorethoxyfos (129), chlorfenapyr (130), chlorfenvinphos (131), chlorfluazuron (132), chlormephos (136), chloroform [CCN], chloropicrin (141), chlorphoxim (989), chlorprazophos (990), chlorpyrifos (145), chlorpyrifos-methyl (146), chlorthiophos (994), chromafenozide (150), cinerin I (696), cinerin II (696), cinerins (696), cis-resmethrin (alternative name), cismethrin (80), clocythrin (alternative name), cloethocarb (999), closantel (alternative name) [CCN], clothianidin (165), copper acetoarsenite [CCN], copper arsenate [CCN], copper oleate [CCN], coumaphos (174), coumithoate (1006), crotamiton (alternative name) [CCN], crotoxyphos (1010), crufomate (1011), cryolite (alternative name) (177), CS 708 (development code) (1012), cyanofenphos (1019), cyanophos (184), cyanthoate (1020), cyclethrin [CCN], cycloprothrin (188), cyfluthrin (193), cyhalothrin (196), cypermethrin (201), cyphenothrin (206), cyromazine (209), cythioate (alternative name) [CCN], d-limonene (alternative name) [CCN], d-tetramethrin (alternative name) (788), DAEP (1031), dazomet (216), DDT (219), decarbofuran (1034), deltamethrin (223), demephion (1037), demephion-O (1037), demephion-S (1037), demeton (1038), demeton-methyl (224), demeton-O (1038), demeton-O-methyl (224), demeton-S (1038), demeton-S-methyl (224), demeton-S-methylsulphon (1039), diafenthiuron (226), dialifos (1042), diamidafos (1044), diazinon (227), dicapthon (1050), dichlofenthion (1051), dichlorvos (236), dicliphos (alternative name), dicresyl (alternative name) [CCN], dicrotophos (243), dicyclanil (244), dieldrin (1070), diethyl 5-methylpyrazol-3-yl phosphate (IUPAC name) (1076), diflubenzuron (250), dilor (alternative name) [CCN], dimefluthrin [CCN], dimefox (1081), dimetan (1085), dimethoate (262), dimethrin (1083), dimethylvinphos (265), dimetilan (1086), dinex (1089), dinex-diclexine (1089), dinoprop (1093), dinosam (1094), dinoseb (1095), dinotefuran (271), diofenolan (1099), dioxabenzofos (1100), dioxacarb (1101), dioxathion (1102), disulfoton (278), dithicrofos (1108), DNOC (282), doramectin (alternative name) [CCN], DSP (1115), ecdysterone (alternative name) [CCN], EI 1642 (development code) (1118), emamectin (291), emamectin benzoate (291), EMPC (1120), empenthrin (292), endosulfan (294), endothion (1121), endrin (1122), EPBP (1123), EPN (297), epofenonane (1124), eprinomectin (alternative name) [CCN], esfenvalerate (302), etaphos (alternative name) [CCN], ethiofencarb (308), ethion (309), ethiprole (310), ethoate-methyl (1134), ethoprophos (312), ethyl formate (IUPAC name) [CCN], ethyl-DDD (alternative name) (1056), ethylene dibromide (316), ethylene dichloride (chemical name) (1136), ethylene oxide [CCN], etofenprox (319), etrimfos (1142), EXD (1143), famphur (323), fenamiphos (326), fenazaflor (1147), fenchlorphos (1148), fenethacarb (1149), fenfluthrin (1150), fenitrothion (335), fenobucarb (336), fenoxacrim (1153), fenoxycarb (340), fenpirithrin (1155), fenpropathrin (342), fenpyrad (alternative name), fensulfothion (1158), fenthion (346), fenthion-ethyl [CCN], fenvalerate (349), fipronil (354), flonicamid (358), flubendiamide (CAS. Reg. No.: 272451-65-7), flucofuron (1168), flucycloxuron (366), flucythrinate (367), fluenetil (1169), flufenerim [CCN], flufenoxuron (370), flufenprox (1171), flumethrin (372), fluvalinate (1184), FMC 1137 (development code) (1185), fonofos (1191), formetanate (405), formetanate hydrochloride (405), formothion (1192), formparanate (1193), fosmethilan (1194), fospirate (1195), fosthiazate (408), fosthietan (1196), furathiocarb (412), furethrin (1200), gamma-cyhalothrin (197), gamma-HCH (430), guazatine (422), guazatine acetates (422), GY-81 (development code) (423), halfenprox (424), halofenozide (425), HCH (430), HEOD (1070), heptachlor (1211), heptenophos (432), heterophos [CCN], hexaflumuron (439), HHDN (864), hydramethylnon (443), hydrogen cyanide (444), hydroprene (445), hyquincarb (1223), imidacloprid (458), imiprothrin (460), indoxacarb (465), iodomethane (IUPAC name) (542), IPSP (1229), isazofos (1231), isobenzan (1232), isocarbophos (alternative name) (473), isodrin (1235), isofenphos (1236), isolane (1237), isoprocarb (472), isopropyl O-(methoxyaminothiophosphoryl)salicylate (IUPAC name) (473), isoprothiolane (474), isothioate (1244), isoxathion (480), ivermectin (alternative name) [CCN], jasmolin I (696), jasmolin II (696), jodfenphos (1248), juvenile hormone I (alternative name) [CCN], juvenile hormone II (alternative name) [CCN], juvenile hormone III (alternative name) [CCN], kelevan (1249), kinoprene (484), lambda-cyhalothrin (198), lead arsenate [CCN], lepimectin (CCN), leptophos (1250), lindane (430), lirimfos (1251), lufenuron (490), lythidathion (1253), m-cumenyl methylcarbamate (IUPAC name) (1014), magnesium phosphide (IUPAC name) (640), malathion (492), malonoben (1254), mazidox (1255), mecarbam (502), mecarphon (1258), menazon (1260), mephosfolan (1261), mercurous chloride (513), mesulfenfos (1263), metaflumizone (CCN), metam (519), metam-potassium (alternative name) (519), metam-sodium (519), methacrifos (1266), methamidophos (527), methanesulfonyl fluoride (IUPAC/Chemical Abstracts name) (1268), methidathion (529), methiocarb (530), methocrotophos (1273), methomyl (531), methoprene (532), methoquinbutyl (1276), methothrin (alternative name) (533), methoxychlor (534), methoxyfenozide (535), methyl bromide (537), methyl isothiocyanate (543), methylchloroform (alternative name) [CCN], methylene chloride [CCN], metofluthrin [CCN], metolcarb (550), metoxadiazone (1288), mevinphos (556), mexacarbate (1290), milbemectin (557), milbemycin oxime (alternative name) [CCN], mipafox (1293), mirex (1294), monocrotophos (561), morphothion (1300), moxidectin (alternative name) [CCN], naftalofos (alternative name) [CCN], naled (567), naphthalene (IUPAC/Chemical Abstracts name) (1303), NC-170 (development code) (1306), NC-184 (compound code), nicotine (578), nicotine sulfate (578), nifluridide (1309), nitenpyram (579), nithiazine (1311), nitrilacarb (1313), nitrilacarb 1:1 zinc chloride complex (1313), NNI-0101 (compound code), NNI-0250 (compound code), nornicotine (traditional name) (1319), novaluron (585), noviflumuron (586), O-2,5-dichloro-4-iodophenyl O-ethyl ethylphosphonothioate (IUPAC name) (1057), O,O-diethyl O-4-methyl-2-oxo-2H-chromen-7-yl phosphorothioate (IUPAC name) (1074), O,O-diethyl 0-6-methyl-2-propylpyrimidin-4-yl phosphorothioate (IUPAC name) (1075), O,O,O',O'-tetrapropyl dithiopyrophosphate (IUPAC name) (1424), oleic acid (IUPAC name) (593), omethoate (594), oxamyl (602), oxydemetonmethyl (609), oxydeprofos (1324), oxydisulfoton (1325), pp'-DDT (219), paradichlorobenzene [CCN], parathion (615), parathion-methyl (616), penfluoron (alternative name) [CCN], pentachlorophenol (623), pentachlorophenyl laurate (IUPAC name) (623), permethrin (626), petroleum oils (alternative name) (628), PH 60-38 (development code) (1328), phenkapton (1330), phenothrin (630), phenthoate (631), phorate (636), phosalone (637), phosfolan (1338), phosmet (638), phosnichlor (1339), phosphamidon (639), phosphine (IUPAC name) (640), phoxim (642), phoxim-methyl (1340), pirimetaphos (1344), pirimicarb (651), pirimiphos-ethyl (1345), pirimiphos-methyl (652), polychlorodicyclopentadiene isomers (IUPAC name) (1346), polychloroterpenes (traditional name) (1347), potassium arsenite [CCN], potassium thiocyanate [CCN], prallethrin (655), precocene I (alternative name) [CCN], precocene OO (alternative name) [CCN], precocene III (alternative name) [CCN], primidophos (1349), profenofos (662), profluthrin [CCN], promacyl (1354), promecarb (1355), propaphos (1356), propetamphos (673), propoxur (678), prothidathion (1360), prothiofos (686), prothoate (1362), protrifenbute [CCN], pymetrozine (688), pyraclofos (689), pyrazophos (693), pyresmethrin (1367), pyrethrin II (696), pyrethrin II (696), pyrethrins (696), pyridaben (699), pyridalyl (700), pyridaphenthion (701), pyrimidifen (706), pyrimitate (1370), pyriproxyfen (708), quassia (alternative name) [CCN], quinalphos (711), quinal-phos-methyl (1376), quinothion (1380), quintiofos (1381), R-1492 (development code) (1382), rafoxanide (alternative name) [CCN], resmethrin (719), rotenone (722), RU 15525 (development code) (723), RU 25475 (development code) (1386), ryania (alternative name) (1387), ryanodine (traditional name) (1387), sabadilla (alternative name) (725), schradan (1389), sebufos (alternative name), selamectin (alternative name) [CCN], SI-0009 (compound code), SI-0205 (compound code), SI-0404 (compound code), SI-0405 (compound code), silafluofen (728), SN 72129 (development code) (1397), sodium arsenite [CCN], sodium cyanide (444), sodium fluoride (IUPAC/Chemical Abstracts name) (1399), sodium hexafluorosilicate (1400), sodium pentachlorophenoxide (623), sodium selenate (IUPAC name) (1401), sodium thiocyanate [CCN], sophamide (1402), spinosad (737), spiromesifen (739), spirotetrmat (CCN), sulcofuron (746), sulcofuron-sodium (746), sulfluramid (750), sulfotep (753), sulfuryl fluoride (756), sulprofos (1408), tar oils (alternative name) (758), tau-fluvalinate (398), tazimcarb (1412), TDE (1414), tebufenozide (762), tebufenpyrad (763), tebupirimfos (764), teflubenzuron (768), tefluthrin (769), temephos (770), TEPP (1417), terallethrin (1418), terbam (alternative name), terbufos (773), tetrachloroethane [CCN], tetrachlorvinphos (777), tetramethrin (787), theta-cypermethrin (204), thiacloprid (791), thiafenox (alternative name), thiamethoxam (792), thicrofos (1428), thiocarboxime (1431), thiocyclam (798), thiocyclam hydrogen oxalate (798), thiodicarb (799), thiofanox (800), thiometon (801), thionazin (1434), thiosultap (803), thiosultap-sodium (803), thuringiensin (alternative name) [CCN], tolfenpyrad (809), tralomethrin (812), transfluthrin (813), transpermethrin (1440), triamiphos (1441), triazamate (818), triazophos (820), triazuron (alternative name), trichlorfon (824), trichlormetaphos-3 (alternative name) [CCN], trichloronat (1452), trifenofos (1455), triflumuron (835), trimethacarb (840), triprene (1459), vamidothion (847), vaniliprole [CCN], veratridine (alternative name) (725), veratrine (alternative name) (725), XMC (853), xylylcarb (854), YI-5302 (compound code), zetacypermethrin (205), zetamethrin (alternative name), zinc phosphide (640), zolaprofos (1469) and ZXI 8901 (development code) (858), a molluscicide selected from the group of substances consisting of bis(tributyltin) oxide (IUPAC name) (913), bromoacetamide [CCN], calcium arsenate [CCN], cloethocarb (999), copper acetoarsenite [CCN], copper sulfate (172), fentin (347), ferric phosphate (IUPAC name) (352), metaldehyde (518), methiocarb (530), niclosamide (576), niclosamide-olamine (576), pentachlorophenol (623), sodium pentachlorophenoxide (623), tazimcarb (1412), thiodicarb (799), tributyltin oxide (913), trifenmorph (1454), trimethacarb (840), triphenyltin acetate (IUPAC name) (347) and triphenyltin hydroxide (IUPAC name) (347), a nematicide selected from the group of substances consisting of AKD-3088 (compound code), 1,2-dibromo-3-chloropropane (IUPAC/Chemical Abstracts name) (1045), 1,2-dichloropropane (IUPAC/Chemical Abstracts name) (1062), 1,2-dichloropropane with 1,3-dichloropropene (IUPAC name) (1063), 1,3-dichloropropene (233), 3,4-dichlorotetrahydrothiophene 1,1-dioxide (IUPAC/Chemical Abstracts name) (1065), 3-(4-chlorophenyl)-5-methylrhodanine (IUPAC name) (980), 5-methyl-6-thioxo-1,3,5-thiadiazinan-3-ylacetic acid (IUPAC name) (1286), 6-isopentenylaminopurine (alternative name) (210), abamectin (1), acetoprole [CCN], alanycarb (15), aldicarb (16), aldoxycarb (863), AZ 60541 (compound code), benclothiaz [CCN], benomyl (62), butylpyridaben (alternative name), cadusafos (109), carbofuran (118), carbon disulfide (945), carbosulfan (119), chloropicrin (141), chlorpyrifos (145), cloethocarb (999), cytokinins (alternative name) (210), dazomet (216), DBCP (1045), DCIP (218), diamidafos (1044), dichlofenthion (1051), dicliphos (alternative name), dimethoate (262), doramectin (alternative name) [CCN], emamectin (291), emamectin benzoate (291), eprinomectin (alternative name) [CCN], ethoprophos (312), ethylene dibromide (316), fenamiphos (326), fenpyrad (alternative name), fensulfothion (1158), fosthiazate (408), fosthietan (1196), furfural (alternative name) [CCN], GY-81 (development code) (423), heterophos [CCN], iodomethane (IUPAC name) (542), isamidofos (1230), isazofos (1231), ivermectin (alternative name) [CCN], kinetin (alternative name) (210), mecarphon (1258), metam (519), metam-potassium (alternative name) (519), metam-sodium (519), methyl bromide (537), methyl isothiocyanate (543), milbemycin oxime (alternative name) [CCN], moxidectin (alternative name) [CCN], *Myrothecium verrucaria* composition (alternative name) (565), NC-184 (compound code), oxamyl (602), phorate (636), phosphamidon (639), phosphocarb [CCN], sebufos (alternative name), selamectin (alternative name) [CCN], spinosad (737), terbam (alternative name), terbufos (773), tetrachlorothiophene (IUPAC/Chemical Abstracts name) (1422), thiafenox (alternative name), thionazin (1434), triazophos (820), triazuron (alternative name), xylenols [CCN], YI-5302 (compound code) and zeatin (alternative name) (210), a nitrification inhibitor selected from the group of substances consisting of potassium ethylxanthate [CCN] and nitrapyrin (580), a plant activator selected from the group of substances consisting of acibenzolar (6), acibenzolar-S-methyl (6), probenazole (658) and *Reynoutria sachalinensis* extract (alternative name) (720), a rodenticide selected from the group of substances consisting of 2-isovalerylindan-1,3-dione (IUPAC name) (1246), 4-(quinoxalin-2-ylamino)benzenesulfonamide (IUPAC name) (748), alpha-chlorohydrin [CCN], aluminium phosphide (640), antu (880), arsenous oxide (882), barium carbonate (891), bisthiosemi (912), brodifacoum (89), bromadiolone (91), bromethalin (92), calcium cyanide (444), chloralose (127), chlorophacinone (140), cholecalciferol (alternative name) (850), coumachlor (1004), coumafuryl (1005), coumatetralyl (175), crimidine (1009), difenacoum (246), difethialone (249), diphacinone (273), ergocalciferol (301), flocoumafen (357), fluoroacetamide (379), flupropadine (1183), flupropadine hydrochloride (1183), gamma-HCH (430), HCH (430), hydrogen cyanide (444), iodomethane (IUPAC name) (542), lindane (430), magnesium phosphide (IUPAC name) (640), methyl bromide (537), norbormide (1318), phosacetim (1336), phosphine (IUPAC name) (640), phosphorus [CCN], pindone (1341), potassium arsenite [CCN], pyrinuron (1371), scilliroside (1390), sodium arsenite [CCN], sodium cyanide (444), sodium fluoroacetate (735), strychnine (745), thallium sulfate [CCN], warfarin (851) and zinc phosphide (640), a synergist selected from the group of substances consisting of 2-(2-butoxyethoxy)-ethyl piperonylate (IUPAC name) (934), 5-(1,3-benzodioxol-5-yl)-3-hexylcyclohex-2-enone (IUPAC name) (903), farnesol with nerolidol (alternative name) (324), MB-599 (development code) (498), MGK 264 (development code) (296), piperonyl butoxide (649), piprotal (1343), propyl isomer (1358), S421 (development code) (724), sesamex (1393), sesasmolin (1394) and sulfoxide (1406), an animal repellent selected from the group of substances consisting of anthraquinone (32), chloralose (127), copper naphthenate [CCN], copper oxychloride (171), diazinon (227), dicyclopentadiene (chemical name) (1069), guazatine (422), guazatine acetates (422), methiocarb (530), pyridin-4-amine (IUPAC name) (23), thiram (804), trimethacarb (840), zinc naphthenate [CCN] and ziram (856), a virucide selected from the group of substances consisting of imanin (alternative name) [CCN] and ribavirin (alternative name) [CCN], and a wound protectant selected from the group of substances consisting of mercuric oxide (512), octhilinone (590) and thiophanate-methyl (802), the compound of formula A-1

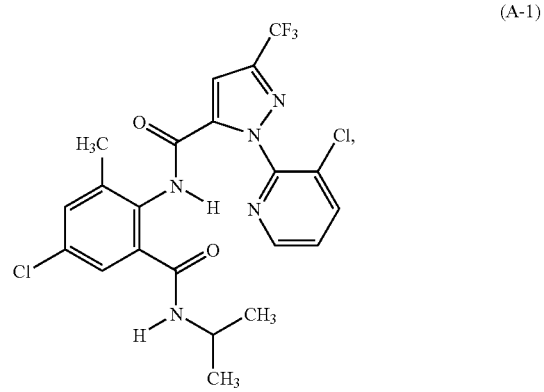

the formula A-2

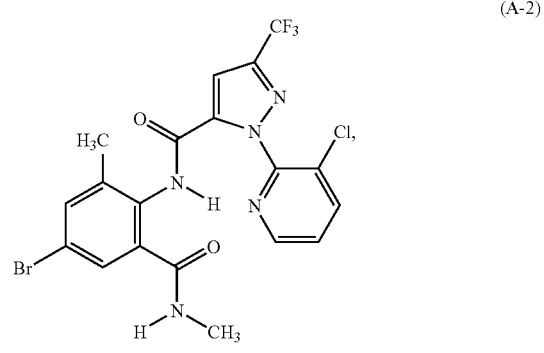

the formula A-3

-continued
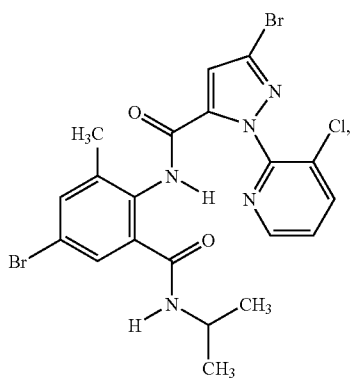
the formula A-4
(A-3)
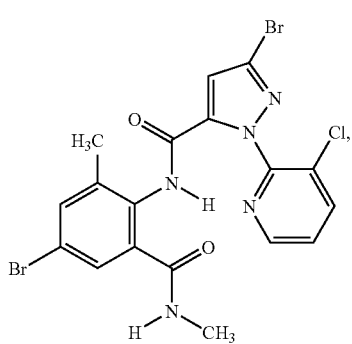
the formula A-5
(A-4)
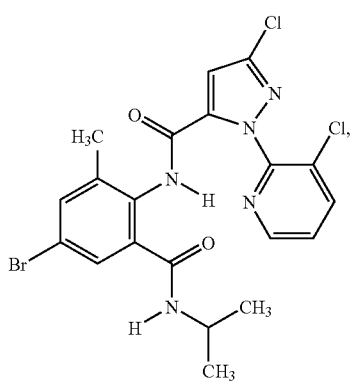
the formula A-6
(A-5)
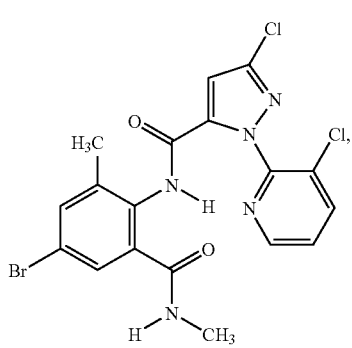
the formula A-7
(A-6)
-continued
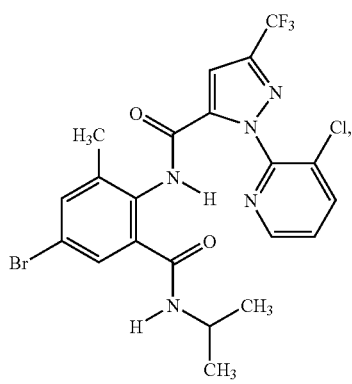
the formula A-8
(A-7)
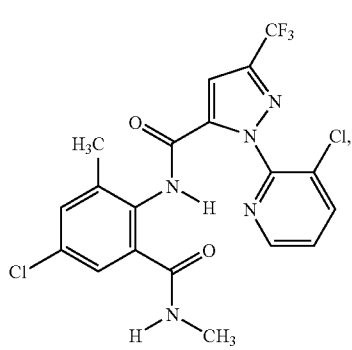
the formula A-9
(A-8)
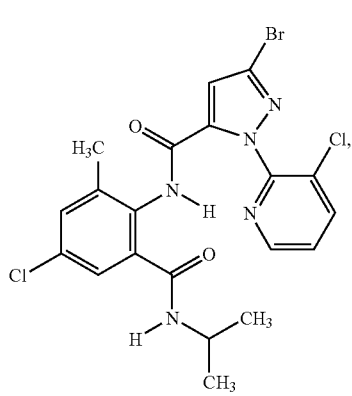
the formula A-10
(A-9)
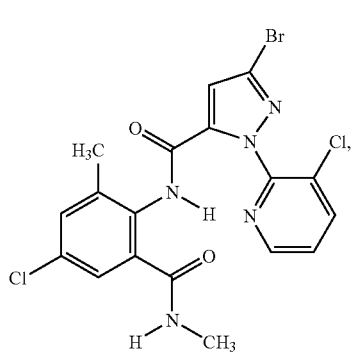
the formula A-11
(A-10)

-continued
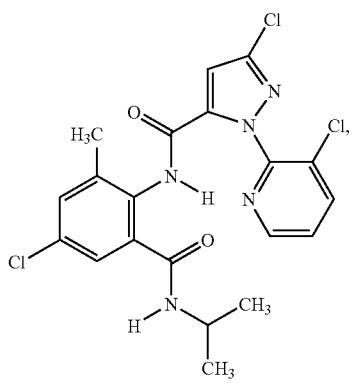
the formula A-12 (A-11)
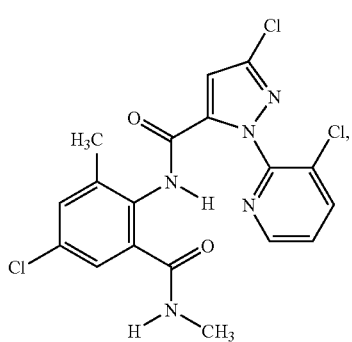
the formula A-13 (A-12)
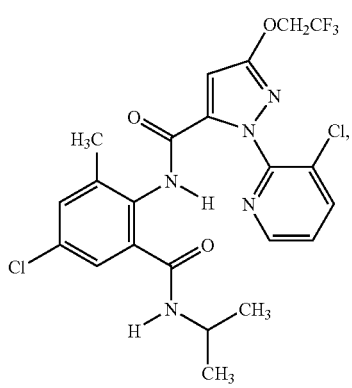
the formula A-14 (A-13)
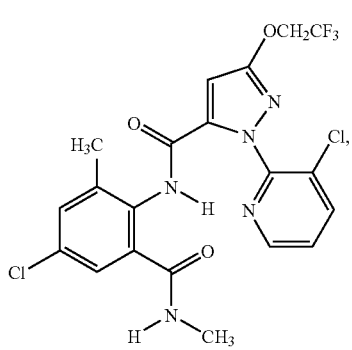
the formula A-15 (A-14)
-continued
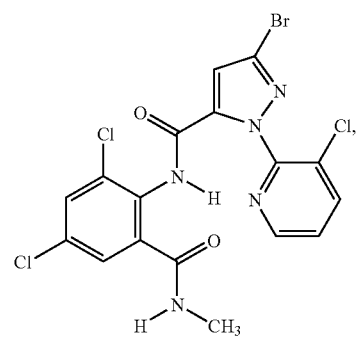
the formula A-16 (A-15)
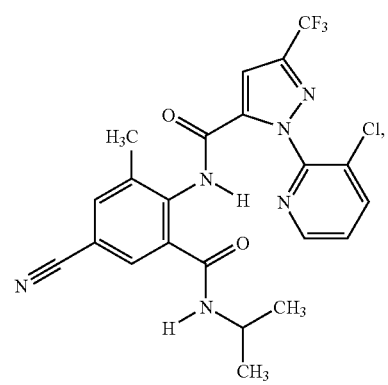
the formula A-17 (A-16)
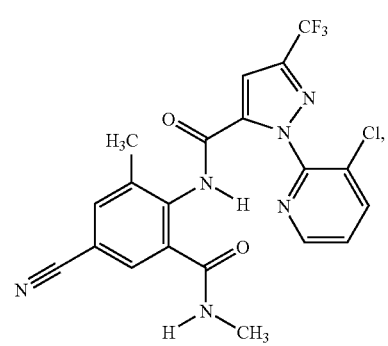
the formula A-18 (A-17)
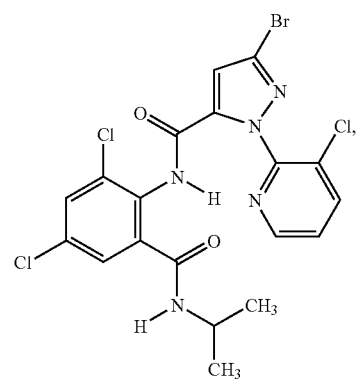
the formula A-19 (A-18)

-continued
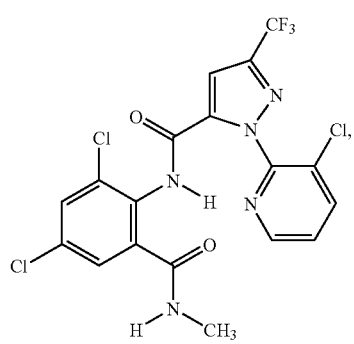
the formula A-20
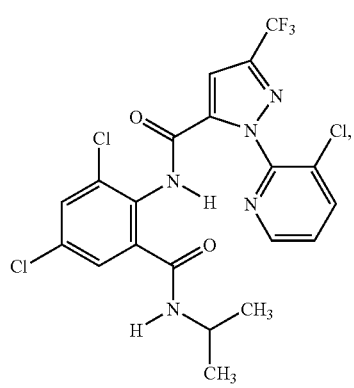
the formula A-21
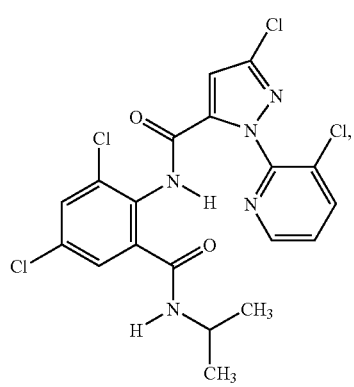
the formula A-22
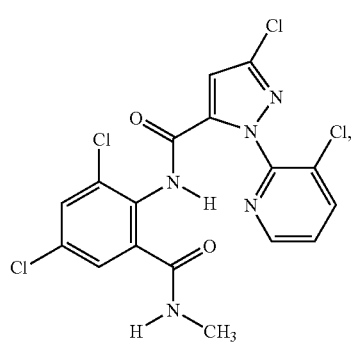
the formula A-23
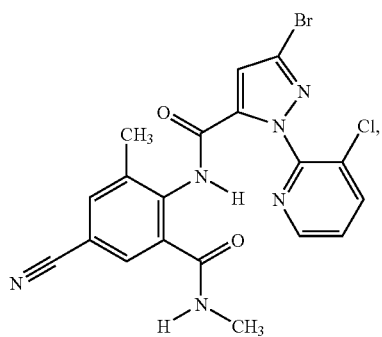
the formula A-24
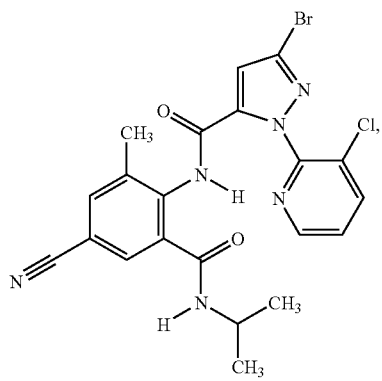
the formula A-25
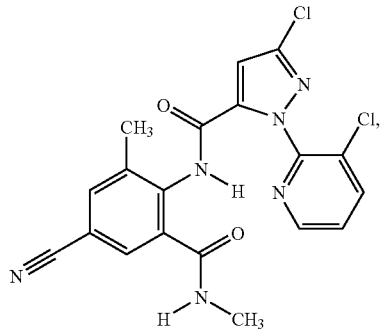
the formula A-26
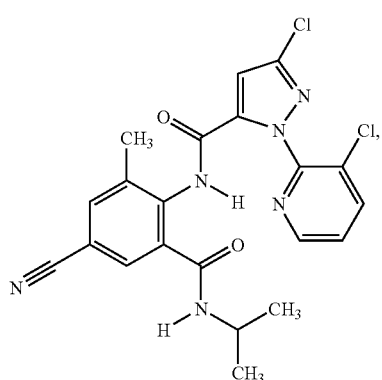
the formula A-27
and fungicides selected from the group consisting of Azaconazole (60207-31-0], Bitertanol [70585-36-3], Bromuconazole [116255-48-2], Cyproconazole [94361-06-5], Difenoconazole [119446-68-3], Diniconazole [83657-24-3], Epoxiconazole [106325-08-0], Fenbuconazole [114369-43-6], Fluquinconazole [136426-54-5], Flusilazole [85509-19-9], Flutriafol [76674-21-0], Hexaconazole [79983-71-4], Imazalil [35554-44-0], Imibenconazole [86598-92-7], Ipconazole [125225-28-7], Metconazole [125116-23-6], Myclobutanil [88671-89-0], Pefurazoate [101903-30-4], Penconazole [66246-88-6], Prothioconazole [178928-70-6], Pyrifenox [88283-41-4], Prochloraz [67747-09-5], Propiconazole [60207-90-1], Simeconazole [149508-90-7], Tebuconazole [107534-96-3], Tetraconazole [112281-77-3], Triadimefon [43121-43-3], Triadimenol [55219-65-3], Triflumizole [99387-89-0], Triticonazole [131983-72-7], Ancymidol [12771-68-5], Fenarimol [60168-88-9], Nuarimol [63284-71-9], Bupirimate [41483-43-6], Dimethirimol [5221-53-4], Ethirimol [23947-60-6], Dodemorph [1593-77-7], Fenpropidine [67306-00-7], Fenpropimorph [67564-91-4], Spiroxamine [118134-30-8], Tridemorph [81412-43-3], Cyprodinil [121552-61-2], Mepanipyrim [110235-47-7], Pyrimethanil [53112-28-0], Fenpiclonil [74738-17-3], Fludioxonil [131341-86-1], Benalaxyl [71626-11-4], Furalaxyl [57646-30-7], Metalaxyl [57837-19-1], R-Metalaxyl [70630-17-0], Ofurace [58810-48-3], Oxadixyl [77732-09-3], Benomyl [17804-35-2], Carbendazim [10605-21-7], Debacarb [62732-91-6], Fuberidazole [3878-19-1], Thiabendazole [148-79-8], Chlozolinate [84332-86-5], Dichlozoline [24201-58-9], Iprodione [36734-19-7], Myclozoline [54864-61-8], Procymidone [32809-16-8], Vinclozoline [50471-44-8], Boscalid [188425-85-6], Carboxin [5234-68-4], Fenfuram [24691-80-3], Flutolanil [66332-96-5], Mepronil [55814-41-0], Oxycarboxin [5259-88-1], Penthiopyrad [183675-82-3], Thifluzamide [130000-40-7], Guazatine [108173-90-6], Dodine [2439-10-3][112-65-2] (freie Base), Iminoctadine [13516-27-3], Azoxystrobin [131860-33-8], Dimoxystrobin [149961-52-4], Enestroburin {Proc. BCPC, Int. Congr., Glasgow, 2003, 1, 93}, Fluoxastrobin [361377-29-9], Kresoxim-methyl [143390-89-0], Metominostrobin [133408-50-1], Trifloxystrobin [141517-21-7], Orysastrobin [248593-16-0], Picoxystrobin [117428-22-5], Pyraclostrobin [175013-18-0], Ferbam [14484-64-1], Mancozeb [8018-01-7], Maneb [12427-38-2], Metiram [9006-42-2], Propineb [12071-83-9], Thiram [137-26-8], Zineb [12122-67-7], Ziram [137-30-4], Captafol [2425-06-1], Captan [133-06-2], Dichlofluanid [1085-98-9], Fluoroimide [41205-21-4], Folpet [133-07-3], Tolylfluanid [731-27-1], Bordeaux Mixture [8011-63-0], Copperhydroxid [20427-59-2], Copperoxychlorid [1332-40-7], Coppersulfat [7758-98-7], Copperoxid [1317-39-1], Mancopper [53988-93-5], Oxine-copper [10380-28-6], Dinocap [131-72-6], Nitrothalisopropyl [10552-74-6], Edifenphos [17109-49-8], Iprobenphos [26087-47-8], Isoprothiolane [50512-35-1], Phosdiphen [36519-00-3], Pyrazophos [13457-18-6], Tolclofos-methyl [57018-04-9], Acibenzolar-5-methyl [135158-54-2], Anilazine [101-05-3], Benthiavalicarb [413615-35-7], Blasticidin-S [2079-00-7], Chinomethionat [2439-01-2], Chloroneb [2675-77-6], Chlorothalonil [1897-45-6], Cyflufenamid [180409-60-3], Cymoxanil [57966-95-7], Dichlone [117-80-6], Diclocymet [139920-32-4], Diclomezine [62865-36-5], Dicloran [99-30-9], Diethofencarb [87130-20-9], Dimethomorph [110488-70-5], SYP-LI90 (Flumorph) [211867-47-9], Dithianon [3347-22-6], Ethaboxam [162650-77-3], Etridiazole [2593-15-9], Famoxadone [131807-57-3], Fenamidone [161326-34-7], Fenoxanil [115852-48-7], Fentin [668-34-8], Ferimzone [89269-64-7], Fluazinam [79622-59-6], Fluopicolide [239110-15-7], Flusulfamide [106917-52-6], Fenhexamid [126833-17-8], Fosetyl-aluminium [39148-24-8], Hymexazol [10004-44-1], Iprovalicarb [140923-17-7], IKF-916 (Cyazofamid) [120116-88-3], Kasugamycin [6980-18-3], Methasulfocarb [66952-49-6], Metrafenone [220899-03-6], Pencycuron [66063-05-6], Phthalide [27355-22-2], Polyoxins [11113-80-7], Probenazole [27605-76-1], Propamocarb [25606-41-1], Proquinazid [189278-12-4], Pyroquilon [57369-32-1], Quinoxyfen [124495-18-7], Quintozene [82-68-8], Schwefel [7704-34-9], Tiadinil [223580-51-6], Triazoxide [72459-58-6], Tricyclazole [41814-78-2], Triforine [26644-46-2], Validamycin [37248-47-8], Zoxamide (RH7281) [156052-68-5], Mandipropamid [374726-62-2], the compound of formula F-1

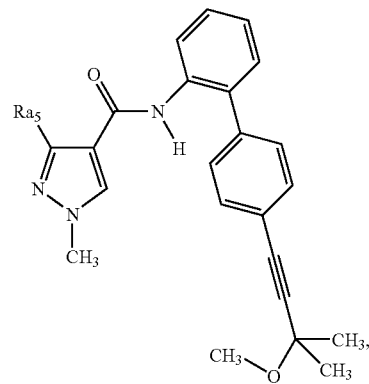

(F-1)

wherein Ra$_5$ is trifluoromethyl or difluoromethyl (WO2004/058723); the compound of formula F-2

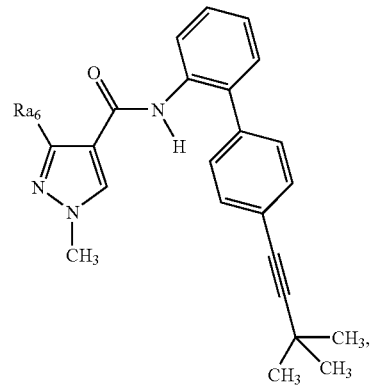

(F-2)

wherein Ra$_6$ is trifluoromethyl or difluoromethyl (WO2004/058723); the racemic compound of formula F-3 (syn)

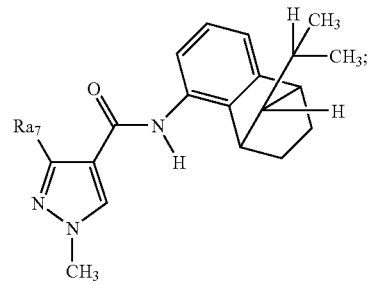

(F-3)

wherein Ra₇ is trifluoromethyl or difluoromethyl (WO2004/035589); the racemic mixture of formula F-4 (anti)

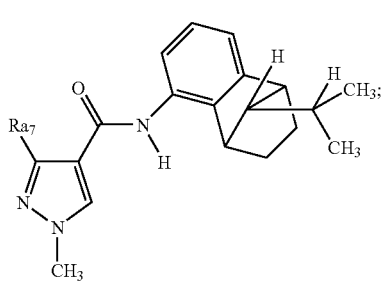
(F-4)

wherein Ra₇ is trifluoromethyl or difluoromethyl (WO2004/035589); the compound of formula F-5

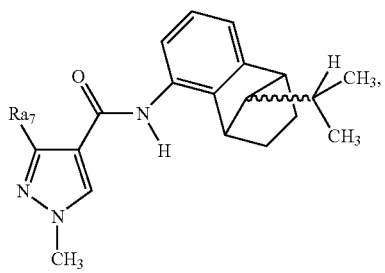
(F-5)

which is an epimeric mixture of racemic compounds of formulae F-3 (syn) and F-4 (anti), wherein the ratio from racemic compounds of formula F-3 (syn) to racemic cmpounds of formula F-4 (anti) is from 1000:1 to 1:1000 and wherein Ra₇ is trifluoromethyl or difluoromethyl (WO2004/035589); the compound of formula F-6

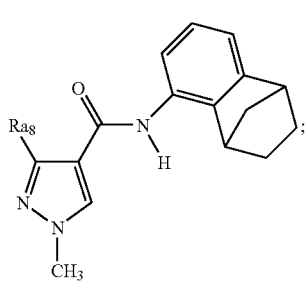
(F-6)

wherein Ra₈ is trifluoromethyl or difluoromethyl (WO2004/035589); the racemic compound of formula F-7 (trans)

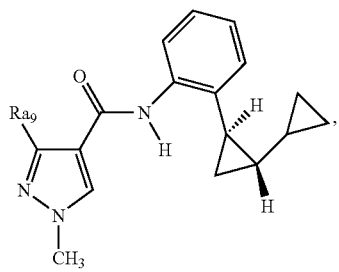
(F-7)

wherein Ra₉ is trifluoromethyl or difluoromethyl (WO03/074491); the racemic compound of formula F-8 (cis)

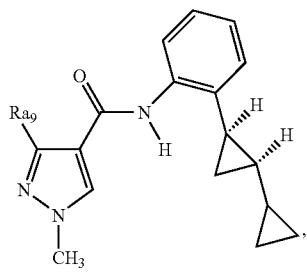
(F-8)

wherein Ra₉ is trifluoromethyl or difluoromethyl (WO03/074491); the compound of formula F-9

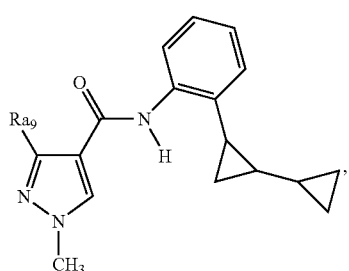
(F-9)

which is a mixture of the racemic compounds of formulae F-7 (trans) and F-8 (cis), wherein the ratio of the racemic compound of formula F-7 (trans) to the racemic compound of formula F-8 (cis) is 2:1 to 100:1; and wherein Rag is trifluoromethyl or difluoromethyl (WO03/074491), the compound of formula F-10

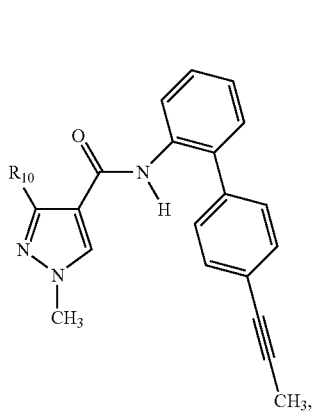
(F-10)

wherein $R_{10}$ is trifluoromethyl or difluoromethyl (WO2004/058723); the racemic compound of formula F-11 (trans)

(F-11)

wherein $R_{11}$ is trifluoromethyl or difluoromethyl (WO03/074491); the racemic compound of formula F-12 (cis)

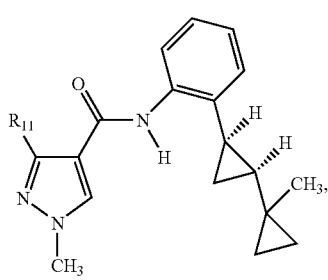
(F-12)

wherein $R_{11}$ is trifluoromethyl or difluoromethyl (WO03/074491); the compound of formula F-13

(F-13)

which is a racemic mixture of the formulae F-11 (trans) and F-12 (cis), and wherein $R_{11}$ is trifluoromethyl or difluoromethyl (WO 03/074491); and the compound of formula F-14

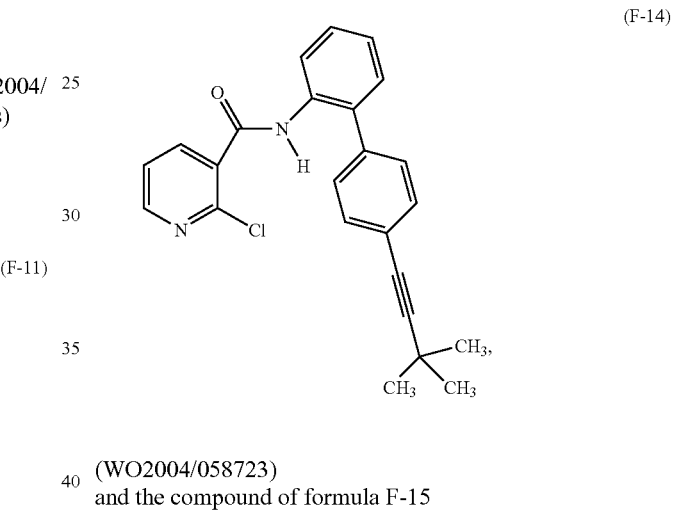
(F-14)

(WO2004/058723)
and the compound of formula F-15

(F-15)

[214706-53-3]

The References in Brackets Behind the Active Ingredients, E.G. [3878-19-1] Refer to the Chemical Abstracts Registry number. The compouds of the formulae A-1 to A-26 are described in WO 03/015518 or in WO 04/067528.

The compounds of the group M are known. Where the compounds of the group M are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood-.net/pesticides/acetoprole.html.

Most of the compounds of the group M are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The following mixtures of the compounds of formula I with one member of the group M are preferred (in the following listing, "M" means one member selected from the group M, so that all mixtures of the following individual compounds of formula I with each member of the group M are specifically described):

T1.1.1+M; T2.+M; T1.1.3+M; T1.4+M; T1.1.5+M; T1.1.6+M; T1.1.7+M; T1.1.8+M; T1.1.9+M; T1.1.10+M; T1.1.11+M; T1.1.12+M; T1.1.13+M; T1.1.14+M; T1.1.15+M; T1.1.16+M; T1.1.17+M; T1.1.18+M; T1.1.19+M; T1.1.20+M; T1.1.21+M; T1.1.22+M; T1.1.23+M; T1.1.24+M; T1.1.25+M; T1.1.26+M; T1.1.27+M; T1.1.28+M; T1.1.29+M; T1.1.30+M; T1.1.31+M; T1.1.32+M; T1.1.33+M; T1.1.34+M; T1.1.35+M; T1.1.36+M; T1.1.37+M; T1.1.38+M; T1.1.39+M; T1.1.40+M; T1.1.41+M; T1.1.42+M; T1.1.43+M; T1.1.44+M; T1.1.45+M; T1.1.46+M; T1.1.47+M; T1.1.48+M; T1.1.49+M; T1.1.50+M; T1.1.51+M; T1.1.52+M; T1.1.53+M; T1.1.54+M; T1.1.55+M; T1.1.56+M; T1.1.57+M; T1.1.58+M; T1.1.59+M; T1.1.60+M; T1.1.61+M; T1.1.62+M; T1.1.63+M; T1.1.64+M; T1.1.65+M; T1.1.66+M; T1.1.67+M; T1.1.68+M; T1.1.69+M; T1.1.70+M; T1.1.71+M; T1.1.72+M; T1.1.73+M; T1.1.74+M; T1.1.75+M; T1.1.76+M; T1.1.77+M; T1.1.78+M; T1.1.79+M; T1.1.80+M; T1.1.81+M; T1.82+M; T1.1.83+M; T1.1.84+M; T1.1.85+M; T1.1.86+M; T1.1.87+M; T1.1.88+M; T1.1.89+M; T1.1.90+M; T1.1.91+M; T1.1.92+M; T1.1.93+M; T1.1.94+M; T1.1.95+M; T1.1.96+M; T1.1.97+M; T1.1.98+M; T1.1.99+M; T1.1.100+M; T1.1.01+M; T1.1.102+M; T1.1.103+M; T1.1.104+M; T1.1.105+M; T1.1.106+M; T1.1.107+M; T1.1.108+M; T1.1.109+M; T1.1.110+M; T1.1.111+M; T1.1.112+M; T1.1.113+M; T1.1.114+M; T1.1.115+M; T1.116+M; T1.1.117+M; T1.1.118+M; T1.1.119+M; T1.1.120+M; T1.1.121+M; T1.1.122+M; T1.1.123+M; T1.1.124+M; T1.1.125+M; T1.1.126+M; T1.1.127+M; T1.1.128+M; T1.1.129+M; T1.1.130+M; T1.1.131+M; T1.1.132+M; T1.1.133+M; T1.1.134+M; T1.1.135+M; T1.1.136+M; T1.1.137+M; T1.1.138+M; T1.1.139+M; T1.1.140+M; T1.1.141+M; T1.1.142+M; T1.1.143+M; T1.1.144+M; T1.1.145+M; T1.1.146+M; T1.1.147+M; T1.1.148+M; T1.1.149+M; T1.1.150+M; T1.1.151+M; T1.1.152+M; T1.1.153+M; T1.54+M; T1.1.155+M; T1.1.156+M; T1.1.157+M; T1.1.158+M; T1.1.159+M; T1.1.160+M; T1.1.161+M; T1.1.162+M; T1.1.163+M; T1.1.164+M; T1.1.165+M; T1.1.166+M; T1.1.167+M; T1.1.168+M; T1.1.169+M; T1.1.170+M; T1.1.171+M; T1.1.172+M; T1.1.173+M; T1.1.174+M; T1.1.175+M; T1.1.176+M; T1.1.177+M; T1.1.178+M; T1.1.179+M; T1.1.180+M; T1.1.181+M; T1.1.182+M; T1.183+M; T1.1.184+M; T1.1.185+M; T1.1.186+M; T1.1.187+M; T1.1.188+M; T1.1.189+M; T1.1.190+M; T1.1.191+M; T1.1.192+M; T1.1.193+M; T1.1.194+M; T1.1.195+M; T1.1.196+M; T1.1.197+M; T1.98+M; T1.1.199+M; T1.1.200+M; T1.1.201+M; T1.1.202+M; T1.1.203+M; T1.1.204+M; T1.1.205+M; T1.1.206+M; T1.1.207+M; T1.1.208+M; T1.1.209+M; T1.1.210+M; T1.1.211+M; T1.1.212+M; T1.1.213+M; T1.1.214+M; T1.1.215+M; T1.1.216+M; T1.1.217+M; T1.1.218+M; T1.1.219+M; T1.1.220+M; T1.1.221+M; T1.1.222+M; T1.1.223+M; T1.1.224+M; T1.1.225+M; T1.1.226+M; T1.1.227+M; T1.1.228+M; T1.1.229+M; T1.1.230+M; T1.1.231+M; T1.1.232+M; T1.1.233+M; T1.1.234+M; T1.1.235+M; T1.1.236+M; T1.1.237+M; T1.1.238+M; T1.1.239+M; T1.1.240+M; T1.1.241+M; T1.1.242+M; T1.1.243+M; T1.1.244+M; T1.1.245+M; T1.1.246+M; T1.1.247+M; T1.1.248+M; T1.1.249+M; T1.1.250+M; T1.1.251+M; T1.1.252+M; T1.1.253+M; T1.1.254+M; T1.1.255+M; T1.1.256+M; T1.1.257+M; T1.1.258+M; T1.1.259+M; T1.1.260+M; T1.1.261+M; T1.1.262+M; T1.1.263+M; T1.1.264+M; T1.1.265+M; T1.1.266+M; T1.1.267+M; T1.1.268+M; T1.1.269+M and T1.1.270+M.

The mixtures comprising a compound of formula I and one or more compounds of the group M can be applied, for example in a single "ready-mix" form, in a combined spray mixture composed from separate formulations of the single active ingredient components, such as a "tank-mix", and also in a combined use of the single active ingredients when applied in a sequential manner, i.e. one after the other with a reasonably short period, such as a few hours or days. The order of applying the components (I) and (M) is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

PREPARATION EXAMPLES

Example P1

Preparation of Compound No. T1.1.1 from Compound No. T55.1.1

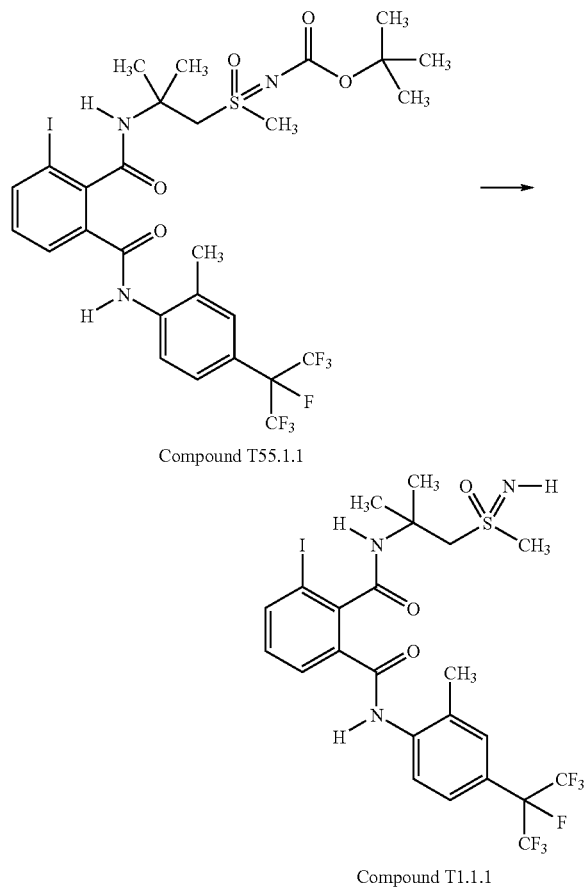

600 mg of compound T55.1.1 is dissolved in 5 ml dichloromethane and cooled with an ice bath to a temperature of 0° C. Then 875 mg trifluoroacetic acid is added dropwise and the reaction mixture is stirred for 3 hours at ambient temperature. Then 10 ml toluene is added the reaction mixture is concentrated under reduced pressure. The residue is solved in a mixture of dichloromethane and water and then neutralised with a sodium carbonate solution. The aqueous phase is extracted several times with dichloromethane. The combined organic phases are dried with MgSO$_4$ and concentrated. The residue is recrystallised in a mixture of ethyl acetate and dichloromethane, there being obtained compound T1.1.1 in form of white cyristals with a melting point of 166-167° C.

Example P2

Preparation of Compound No. T55.1.1

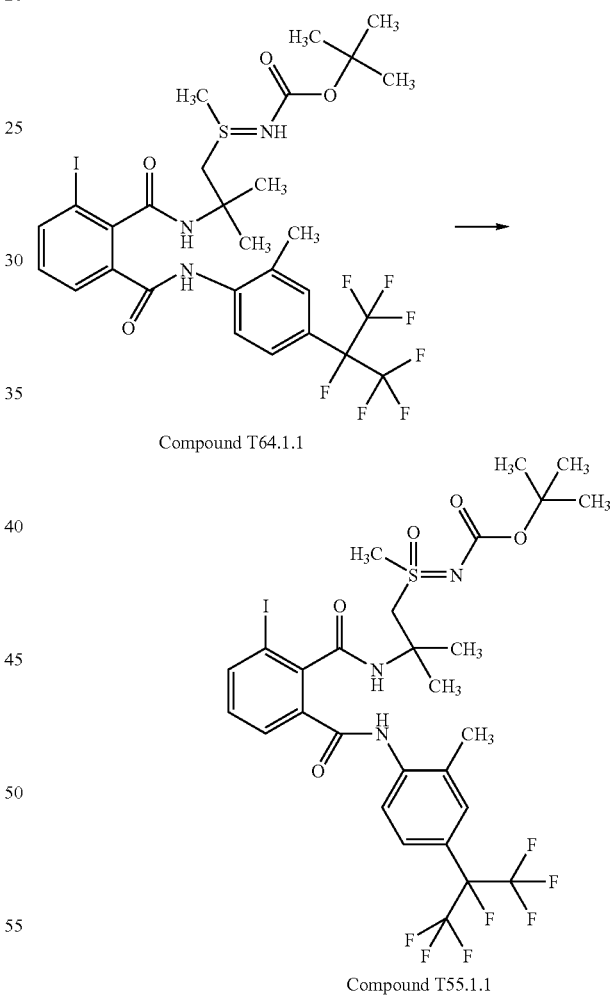

1 g of compound T64.1.1 is dissolved in 10 ml dichloromethane and then 3.4 mg ruthenium (IV) oxide hydrate is added. Then a solution of 559 mg sodium (meta) periodate dissolved in 5 ml of water is added dropwise and the reaction mixture is stirred for 30 minutes. After this period the aqueous phase is separated and 1 ml isopropanole is added to the dichloromethane phase. This mixture is stirred for 15 minutes at ambient temperature whereby a grey suspension is formed.

This suspension is filtered over Hyflo, then the filtrate is dried over MgSO₄ and the solvent is concentrated by evaporation. The residue is purified with HPLC, firstly with hexane:ethyl acetate 3:1, with increasing ethyl acetate as eluent to 100% within 15 minutes, there being obtained the product T 55.1.1 in form of an oil, which becomes solid.

Example P3

Preparation of compound T64.1.1

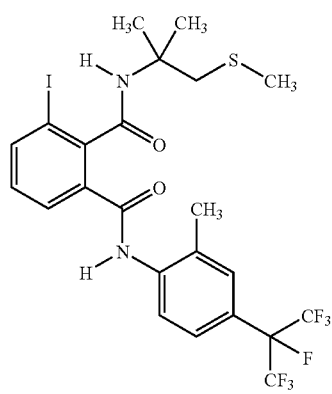

Compound D

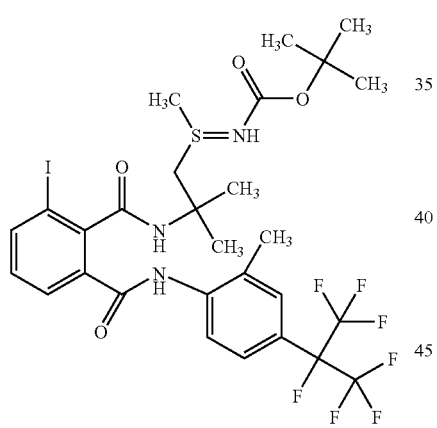

Compound T64.1.1

2.8 g of known compound D is dissolved in 60 ml 2,2,2-trifluoroethanol and cooled to a temperature of –40° C. At this temperature 1.11 g N-tert-butyloxycarbonyl-3-(4-cyanophenyl)oxaziridine is added and the reaction mixture is stirred at a temperature of –40° C. for 3 hours. Then the reaction mixture is concentrated by evaporation and the residue is purified with HPLC, firstly with hexane:ethyl acetate 3:1, with increasing ethyl acetate as eluent to 100% within 15 minutes, there being obtained the product T 64.1.1 in solid form with a melting point of 125-126° C.

The compounds listed in the following Table P can be prepared analogous to the procedures described above (m.p.=melting point in ° C.):

TABLE P

Compounds of formula I:

| No. | Structure | Phys. Data |
|---|---|---|
| T64.1.136 | 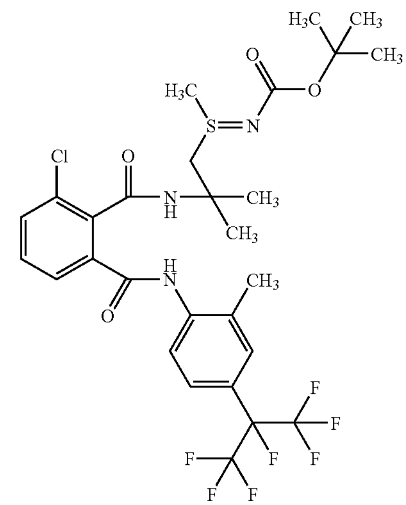 | m.p. 103 |
| T55.1.136 | 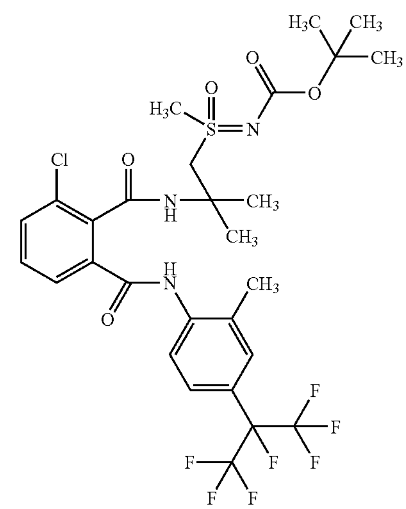 | m.p. 113-114 |
| T1.1.136 | 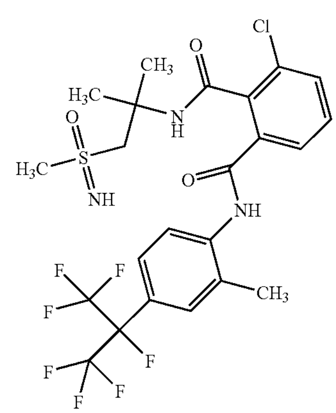 | m.p. 87-88 |

TABLE P-continued

Compounds of formula I:

| No. | Structure | Phys. Data |
|---|---|---|
| T64.1.1 | 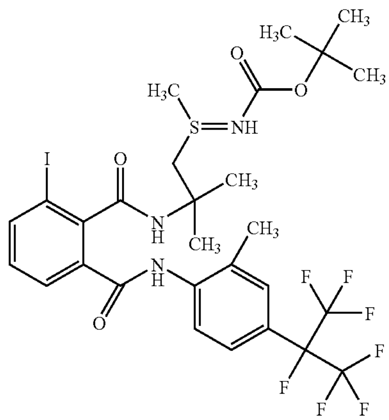 | m.p. 125-126 |
| T55.1.1 | 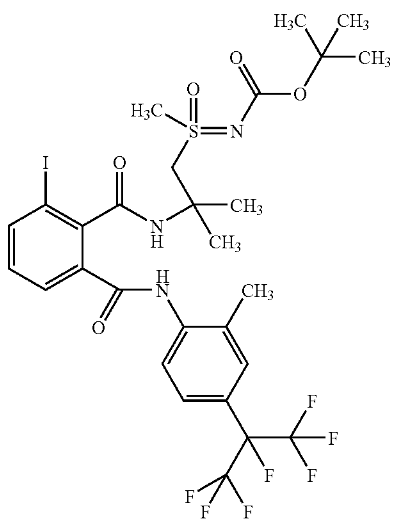 | 804 (M + 23)+ |
| T1.1.1 | 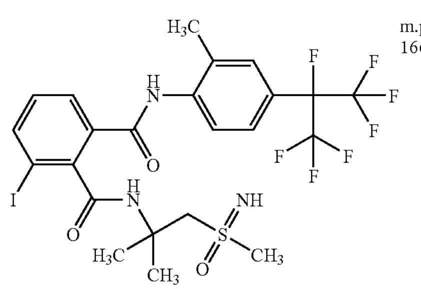 | m.p. 166-167 |

The examples which follow are intended to illustrate the invention and show preferred compounds of formula I. They do not limit the invention. Temperatures are given in degrees Celsius. The abbreviation "M. P." means "melting point".

The Table A discloses 270 meanings of the variables $R_1$, $S_1$, $S_3$ and $Y_1$ in a compound of the formula I-A. The left side of the meanings of substituent $Y_1$ binds to the nitrogen atom, the right side to the sulfur atom.

TABLE A (I-A)

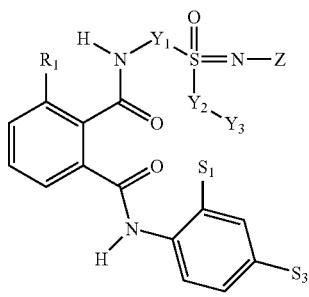

| Line | $R_1$ | $S_1$ | $S_3$ | $Y_1$ |
|---|---|---|---|---|
| A.1.1 | I | Me | $CF(CF_3)_2$ | $C(CH_3)_2CH_2$ |
| A.1.2 | I | Me | $CF(CF_3)_2$ | $C(CH_3)_2(CH_2)_2$ |
| A.1.3 | I | Me | $CF(CF_3)_2$ | $C(CH_3)_2(CH_2)_3$ |
| A.1.4 | I | Me | $CF(CF_3)_2$ | $C(CH_3)_2(CH_2)_4$ |
| A.1.5 | I | Me | $CF(CF_3)_2$ | $CH(CH_3)$ |
| A.1.6 | I | Me | $CF(CF_3)_2$ | $CH(CH_3)CH_2$ |
| A.1.7 | I | Me | $CF(CF_3)_2$ | $CH(CH_3)(CH_2)_2$ |
| A.1.8 | I | Me | $CF(CF_3)_2$ | $CH(CH_3)(CH_2)_3$ |
| A.1.9 | I | Me | $CF(CF_3)_2$ | $CH(CH_3)(CH_2)_4$ |
| A.1.10 | I | Me | $OCF_3$ | $C(CH_3)_2CH_2$ |
| A.1.11 | I | Me | $OCF_3$ | $C(CH_3)_2(CH_2)_2$ |
| A.1.12 | I | Me | $OCF_3$ | $C(CH_3)_2(CH_2)_3$ |
| A.1.13 | I | Me | $OCF_3$ | $C(CH_3)_2(CH_2)_4$ |
| A.1.14 | I | Me | $OCF_3$ | $CH(CH_3)$ |
| A.1.15 | I | Me | $OCF_3$ | $CH(CH_3)CH_2$ |
| A.1.16 | I | Me | $OCF_3$ | $CH(CH_3)(CH_2)_2$ |
| A.1.17 | I | Me | $OCF_3$ | $CH(CH_3)(CH_2)_3$ |
| A.1.18 | I | Me | $OCF_3$ | $CH(CH_3)(CH_2)_4$ |
| A.1.19 | I | Me | $CF_3$ | $C(CH_3)_2CH_2$ |
| A.1.20 | I | Me | $CF_3$ | $C(CH_3)_2(CH_2)_2$ |
| A.1.21 | I | Me | $CF_3$ | $C(CH_3)_2(CH_2)_3$ |
| A.1.22 | I | Me | $CF_3$ | $C(CH_3)_2(CH_2)_4$ |
| A.1.23 | I | Me | $CF_3$ | $CH(CH_3)$ |
| A.1.24 | I | Me | $CF_3$ | $CH(CH_3)CH_2$ |
| A.1.25 | I | Me | $CF_3$ | $CH(CH_3)(CH_2)_2$ |
| A.1.26 | I | Me | $CF_3$ | $CH(CH_3)(CH_2)_3$ |
| A.1.27 | I | Me | $CF_3$ | $CH(CH_3)(CH_2)_4$ |
| A.1.28 | I | Me | $CF_2CF_3$ | $C(CH_3)_2CH_2$ |
| A.1.29 | I | Me | $CF_2CF_3$ | $C(CH_3)_2(CH_2)_2$ |
| A.1.30 | I | Me | $CF_2CF_3$ | $C(CH_3)_2(CH_2)_3$ |
| A.1.31 | I | Me | $CF_2CF_3$ | $C(CH_3)_2(CH_2)_4$ |
| A.1.32 | I | Me | $CF_2CF_3$ | $CH(CH_3)$ |
| A.1.33 | I | Me | $CF_2CF_3$ | $CH(CH_3)CH_2$ |
| A.1.34 | I | Me | $CF_2CF_3$ | $CH(CH_3)(CH_2)_2$ |
| A.1.35 | I | Me | $CF_2CF_3$ | $CH(CH_3)(CH_2)_3$ |
| A.1.36 | I | Me | $CF_2CF_3$ | $CH(CH_3)(CH_2)_4$ |
| A.1.37 | I | Me | $CH(CF_3)_2$ | $C(CH_3)_2CH_2$ |
| A.1.38 | I | Me | $CH(CF_3)_2$ | $C(CH_3)_2(CH_2)_2$ |
| A.1.39 | I | Me | $CH(CF_3)_2$ | $C(CH_3)_2(CH_2)_3$ |
| A.1.40 | I | Me | $CH(CF_3)_2$ | $C(CH_3)_2(CH_2)_4$ |
| A.1.41 | I | Me | $CH(CF_3)_2$ | $CH(CH_3)$ |
| A.1.42 | I | Me | $CH(CF_3)_2$ | $CH(CH_3)CH_2$ |
| A.1.43 | I | Me | $CH(CF_3)_2$ | $CH(CH_3)(CH_2)_2$ |
| A.1.44 | I | Me | $CH(CF_3)_2$ | $CH(CH_3)(CH_2)_3$ |
| A.1.45 | I | Me | $CH(CF_3)_2$ | $CH(CH_3)(CH_2)_4$ |
| A.1.46 | I | Cl | $CF(CF_3)_2$ | $C(CH_3)_2CH_2$ |
| A.1.47 | I | Cl | $CF(CF_3)_2$ | $C(CH_3)_2(CH_2)_2$ |
| A.1.48 | I | Cl | $CF(CF_3)_2$ | $C(CH_3)_2(CH_2)_3$ |
| A.1.49 | I | Cl | $CF(CF_3)_2$ | $C(CH_3)_2(CH_2)_4$ |
| A.1.50 | I | Cl | $CF(CF_3)_2$ | $CH(CH_3)$ |
| A.1.51 | I | Cl | $CF(CF_3)_2$ | $CH(CH_3)CH_2$ |
| A.1.52 | I | Cl | $CF(CF_3)_2$ | $CH(CH_3)(CH_2)_2$ |
| A.1.53 | I | Cl | $CF(CF_3)_2$ | $CH(CH_3)(CH_2)_3$ |
| A.1.54 | I | Cl | $CF(CF_3)_2$ | $CH(CH_3)(CH_2)_4$ |
| A.1.55 | I | Cl | $OCF_3$ | $C(CH_3)_2CH_2$ |
| A.1.56 | I | Cl | $OCF_3$ | $C(CH_3)_2(CH_2)_2$ |
| A.1.57 | I | Cl | $OCF_3$ | $C(CH_3)_2(CH_2)_3$ |
| A.1.58 | I | Cl | $OCF_3$ | $C(CH_3)_2(CH_2)_4$ |
| A.1.59 | I | Cl | $OCF_3$ | $CH(CH_3)$ |
| A.1.60 | I | Cl | $OCF_3$ | $CH(CH_3)CH_2$ |
| A.1.61 | I | Cl | $OCF_3$ | $CH(CH_3)(CH_2)_2$ |

TABLE A-continued (I-A)

| Line | R₁ | S₁ | S₃ | Y₁ |
|---|---|---|---|---|
| A.1.62 | I | Cl | OCF$_3$ | CH(CH$_3$)(CH$_2$)$_3$ |
| A.1.63 | I | Cl | OCF$_3$ | CH(CH$_3$)(CH$_2$)$_4$ |
| A.1.64 | I | Cl | CF$_3$ | C(CH$_3$)$_2$CH$_2$ |
| A.1.65 | I | Cl | CF$_3$ | C(CH$_3$)$_2$(CH$_2$)$_2$ |
| A.1.66 | I | Cl | CF$_3$ | C(CH$_3$)$_2$(CH$_2$)$_3$ |
| A.1.67 | I | Cl | CF$_3$ | C(CH$_3$)$_2$(CH$_2$)$_4$ |
| A.1.68 | I | Cl | CF$_3$ | CH(CH$_3$) |
| A.1.69 | I | Cl | CF$_3$ | CH(CH$_3$)CH$_2$ |
| A.1.70 | I | Cl | CF$_3$ | CH(CH$_3$)(CH$_2$)$_2$ |
| A.1.71 | I | Cl | CF$_3$ | CH(CH$_3$)(CH$_2$)$_3$ |
| A.1.72 | I | Cl | CF$_3$ | CH(CH$_3$)(CH$_2$)$_4$ |
| A.1.73 | I | Cl | CF$_2$CF$_3$ | C(CH$_3$)$_2$CH$_2$ |
| A.1.74 | I | Cl | CF$_2$CF$_3$ | C(CH$_3$)$_2$(CH$_2$)$_2$ |
| A.1.75 | I | Cl | CF$_2$CF$_3$ | C(CH$_3$)$_2$(CH$_2$)$_3$ |
| A.1.76 | I | Cl | CF$_2$CF$_3$ | C(CH$_3$)$_2$(CH$_2$)$_4$ |
| A.1.77 | I | Cl | CF$_2$CF$_3$ | CH(CH$_3$) |
| A.1.78 | I | Cl | CF$_2$CF$_3$ | CH(CH$_3$)CH$_2$ |
| A.1.79 | I | Cl | CF$_2$CF$_3$ | CH(CH$_3$)(CH$_2$)$_2$ |
| A.1.80 | I | Cl | CF$_2$CF$_3$ | CH(CH$_3$)(CH$_2$)$_3$ |
| A.1.81 | I | Cl | CF$_2$CF$_3$ | CH(CH$_3$)(CH$_2$)$_4$ |
| A.1.82 | I | Cl | CH(CF$_3$)$_2$ | C(CH$_3$)$_2$CH$_2$ |
| A.1.83 | I | Cl | CH(CF$_3$)$_2$ | C(CH$_3$)$_2$(CH$_2$)$_2$ |
| A.1.84 | I | Cl | CH(CF$_3$)$_2$ | C(CH$_3$)$_2$(CH$_2$)$_3$ |
| A.1.85 | I | Cl | CH(CF$_3$)$_2$ | C(CH$_3$)$_2$(CH$_2$)$_4$ |
| A.1.86 | I | Cl | CH(CF$_3$)$_2$ | CH(CH$_3$) |
| A.1.87 | I | Cl | CH(CF$_3$)$_2$ | CH(CH$_3$)CH$_2$ |
| A.1.88 | I | Cl | CH(CF$_3$)$_2$ | CH(CH$_3$)(CH$_2$)$_2$ |
| A.1.89 | I | Cl | CH(CF$_3$)$_2$ | CH(CH$_3$)(CH$_2$)$_3$ |
| A.1.90 | I | Cl | CH(CF$_3$)$_2$ | CH(CH$_3$)(CH$_2$)$_4$ |
| A.1.91 | I | H | CF(CF$_3$)$_2$ | C(CH$_3$)$_2$CH$_2$ |
| A.1.92 | I | H | CF(CF$_3$)$_2$ | C(CH$_3$)$_2$(CH$_2$)$_2$ |
| A.1.93 | I | H | CF(CF$_3$)$_2$ | C(CH$_3$)$_2$(CH$_2$)$_3$ |
| A.1.94 | I | H | CF(CF$_3$)$_2$ | C(CH$_3$)$_2$(CH$_2$)$_4$ |
| A.1.95 | I | H | CF(CF$_3$)$_2$ | CH(CH$_3$) |
| A.1.96 | I | H | CF(CF$_3$)$_2$ | CH(CH$_3$)CH$_2$ |
| A.1.97 | I | H | CF(CF$_3$)$_2$ | CH(CH$_3$)(CH$_2$)$_2$ |
| A.1.98 | I | H | CF(CF$_3$)$_2$ | CH(CH$_3$)(CH$_2$)$_3$ |
| A.1.99 | I | H | CF(CF$_3$)$_2$ | CH(CH$_3$)(CH$_2$)$_4$ |
| A.1.100 | I | H | OCF$_3$ | C(CH$_3$)$_2$CH$_2$ |
| A.1.101 | I | H | OCF$_3$ | C(CH$_3$)$_2$(CH$_2$)$_2$ |
| A.1.102 | I | H | OCF$_3$ | C(CH$_3$)$_2$(CH$_2$)$_3$ |
| A.1.103 | I | H | OCF$_3$ | C(CH$_3$)$_2$(CH$_2$)$_4$ |
| A.1.104 | I | H | OCF$_3$ | CH(CH$_3$) |
| A.1.105 | I | H | OCF$_3$ | CH(CH$_3$)CH$_2$ |
| A.1.106 | I | H | OCF$_3$ | CH(CH$_3$)(CH$_2$)$_2$ |
| A.1.107 | I | H | OCF$_3$ | CH(CH$_3$)(CH$_2$)$_3$ |
| A.1.108 | I | H | OCF$_3$ | CH(CH$_3$)(CH$_2$)$_4$ |
| A.1.109 | I | H | CF$_3$ | C(CH$_3$)$_2$CH$_2$ |
| A.1.110 | I | H | CF$_3$ | C(CH$_3$)$_2$(CH$_2$)$_2$ |
| A.1.111 | I | H | CF$_3$ | C(CH$_3$)$_2$(CH$_2$)$_3$ |
| A.1.112 | I | H | CF$_3$ | C(CH$_3$)$_2$(CH$_2$)$_4$ |
| A.1.113 | I | H | CF$_3$ | CH(CH$_3$) |
| A.1.114 | I | H | CF$_3$ | CH(CH$_3$)CH$_2$ |
| A.1.115 | I | H | CF$_3$ | CH(CH$_3$)(CH$_2$)$_2$ |
| A.1.116 | I | H | CF$_3$ | CH(CH$_3$)(CH$_2$)$_3$ |
| A.1.117 | I | H | CF$_3$ | CH(CH$_3$)(CH$_2$)$_4$ |
| A.1.118 | I | H | CF$_2$CF$_3$ | C(CH$_3$)$_2$CH$_2$ |
| A.1.119 | I | H | CF$_2$CF$_3$ | C(CH$_3$)$_2$(CH$_2$)$_2$ |
| A.1.120 | I | H | CF$_2$CF$_3$ | C(CH$_3$)$_2$(CH$_2$)$_3$ |
| A.1.121 | I | H | CF$_2$CF$_3$ | C(CH$_3$)$_2$(CH$_2$)$_4$ |
| A.1.122 | I | H | CF$_2$CF$_3$ | CH(CH$_3$) |
| A.1.123 | I | H | CF$_2$CF$_3$ | CH(CH$_3$)CH$_2$ |
| A.1.124 | I | H | CF$_2$CF$_3$ | CH(CH$_3$)(CH$_2$)$_2$ |
| A.1.125 | I | H | CF$_2$CF$_3$ | CH(CH$_3$)(CH$_2$)$_3$ |
| A.1.126 | I | H | CF$_2$CF$_3$ | CH(CH$_3$)(CH$_2$)$_4$ |
| A.1.127 | I | H | CH(CF$_3$)$_2$ | C(CH$_3$)$_2$CH$_2$ |
| A.1.128 | I | H | CH(CF$_3$)$_2$ | C(CH$_3$)$_2$(CH$_2$)$_2$ |
| A.1.129 | I | H | CH(CF$_3$)$_2$ | C(CH$_3$)$_2$(CH$_2$)$_3$ |
| A.1.130 | I | H | CH(CF$_3$)$_2$ | C(CH$_3$)$_2$(CH$_2$)$_4$ |
| A.1.131 | I | H | CH(CF$_3$)$_2$ | CH(CH$_3$) |
| A.1.132 | I | H | CH(CF$_3$)$_2$ | CH(CH$_3$)CH$_2$ |
| A.1.133 | I | H | CH(CF$_3$)$_2$ | CH(CH$_3$)(CH$_2$)$_2$ |
| A.1.134 | I | H | CH(CF$_3$)$_2$ | CH(CH$_3$)(CH$_2$)$_3$ |
| A.1.135 | I | H | CH(CF$_3$)$_2$ | CH(CH$_3$)(CH$_2$)$_4$ |
| A.1.136 | Cl | Me | CF(CF$_3$)$_2$ | C(CH$_3$)$_2$CH$_2$ |
| A.1.137 | Cl | Me | CF(CF$_3$)$_2$ | C(CH$_3$)$_2$(CH$_2$)$_2$ |
| A.1.138 | Cl | Me | CF(CF$_3$)$_2$ | C(CH$_3$)$_2$(CH$_2$)$_3$ |
| A.1.139 | Cl | Me | CF(CF$_3$)$_2$ | C(CH$_3$)$_2$(CH$_2$)$_4$ |
| A.1.140 | Cl | Me | CF(CF$_3$)$_2$ | CH(CH$_3$) |
| A.1.141 | Cl | Me | CF(CF$_3$)$_2$ | CH(CH$_3$)CH$_2$ |
| A.1.142 | Cl | Me | CF(CF$_3$)$_2$ | CH(CH$_3$)(CH$_2$)$_2$ |
| A.1.143 | Cl | Me | CF(CF$_3$)$_2$ | CH(CH$_3$)(CH$_2$)$_3$ |
| A.1.144 | Cl | Me | CF(CF$_3$)$_2$ | CH(CH$_3$)(CH$_2$)$_4$ |
| A.1.145 | Cl | Me | OCF$_3$ | C(CH$_3$)$_2$CH$_2$ |
| A.1.146 | Cl | Me | OCF$_3$ | C(CH$_3$)$_2$(CH$_2$)$_2$ |
| A.1.147 | Cl | Me | OCF$_3$ | C(CH$_3$)$_2$(CH$_2$)$_3$ |
| A.1.148 | Cl | Me | OCF$_3$ | C(CH$_3$)$_2$(CH$_2$)$_4$ |
| A.1.149 | Cl | Me | OCF$_3$ | CH(CH$_3$) |
| A.1.150 | Cl | Me | OCF$_3$ | CH(CH$_3$)CH$_2$ |
| A.1.151 | Cl | Me | OCF$_3$ | CH(CH$_3$)(CH$_2$)$_2$ |
| A.1.152 | Cl | Me | OCF$_3$ | CH(CH$_3$)(CH$_2$)$_3$ |
| A.1.153 | Cl | Me | OCF$_3$ | CH(CH$_3$)(CH$_2$)$_4$ |
| A.1.154 | Cl | Me | CF$_3$ | C(CH$_3$)$_2$CH$_2$ |
| A.1.155 | Cl | Me | CF$_3$ | C(CH$_3$)$_2$(CH$_2$)$_2$ |
| A.1.156 | Cl | Me | CF$_3$ | C(CH$_3$)$_2$(CH$_2$)$_3$ |
| A.1.157 | Cl | Me | CF$_3$ | C(CH$_3$)$_2$(CH$_2$)$_4$ |
| A.1.158 | Cl | Me | CF$_3$ | CH(CH$_3$) |
| A.1.159 | Cl | Me | CF$_3$ | CH(CH$_3$)CH$_2$ |
| A.1.160 | Cl | Me | CF$_3$ | CH(CH$_3$)(CH$_2$)$_2$ |
| A.1.161 | Cl | Me | CF$_3$ | CH(CH$_3$)(CH$_2$)$_3$ |
| A.1.162 | Cl | Me | CF$_3$ | CH(CH$_3$)(CH$_2$)$_4$ |
| A.1.163 | Cl | Me | CF$_2$CF$_3$ | C(CH$_3$)$_2$CH$_2$ |
| A.1.164 | Cl | Me | CF$_2$CF$_3$ | C(CH$_3$)$_2$(CH$_2$)$_2$ |
| A.1.165 | Cl | Me | CF$_2$CF$_3$ | C(CH$_3$)$_2$(CH$_2$)$_3$ |
| A.1.166 | Cl | Me | CF$_2$CF$_3$ | C(CH$_3$)$_2$(CH$_2$)$_4$ |
| A.1.167 | Cl | Me | CF$_2$CF$_3$ | CH(CH$_3$) |
| A.1.168 | Cl | Me | CF$_2$CF$_3$ | CH(CH$_3$)CH$_2$ |
| A.1.169 | Cl | Me | CF$_2$CF$_3$ | CH(CH$_3$)(CH$_2$)$_2$ |
| A.1.170 | Cl | Me | CF$_2$CF$_3$ | CH(CH$_3$)(CH$_2$)$_3$ |
| A.1.171 | Cl | Me | CF$_2$CF$_3$ | CH(CH$_3$)(CH$_2$)$_4$ |
| A.1.172 | Cl | Me | CH(CF$_3$)$_2$ | C(CH$_3$)$_2$CH$_2$ |
| A.1.173 | Cl | Me | CH(CF$_3$)$_2$ | C(CH$_3$)$_2$(CH$_2$)$_2$ |
| A.1.174 | Cl | Me | CH(CF$_3$)$_2$ | C(CH$_3$)$_2$(CH$_2$)$_3$ |
| A.1.175 | Cl | Me | CH(CF$_3$)$_2$ | C(CH$_3$)$_2$(CH$_2$)$_4$ |
| A.1.176 | Cl | Me | CH(CF$_3$)$_2$ | CH(CH$_3$) |
| A.1.177 | Cl | Me | CH(CF$_3$)$_2$ | CH(CH$_3$)CH$_2$ |
| A.1.178 | Cl | Me | CH(CF$_3$)$_2$ | CH(CH$_3$)(CH$_2$)$_2$ |
| A.1.179 | Cl | Me | CH(CF$_3$)$_2$ | CH(CH$_3$)(CH$_2$)$_3$ |
| A.1.180 | Cl | Me | CH(CF$_3$)$_2$ | CH(CH$_3$)(CH$_2$)$_4$ |
| A.1.181 | Cl | Cl | CF(CF$_3$)$_2$ | C(CH$_3$)$_2$CH$_2$ |
| A.1.182 | Cl | Cl | CF(CF$_3$)$_2$ | C(CH$_3$)$_2$(CH$_2$)$_2$ |
| A.1.183 | Cl | Cl | CF(CF$_3$)$_2$ | C(CH$_3$)$_2$(CH$_2$)$_3$ |

TABLE A-continued (I-A)

| Line | $R_1$ | $S_1$ | $S_3$ | $Y_1$ |
|---|---|---|---|---|
| A.1.184 | Cl | Cl | $CF(CF_3)_2$ | $C(CH_3)_2(CH_2)_4$ |
| A.1.185 | Cl | Cl | $CF(CF_3)_2$ | $CH(CH_3)$ |
| A.1.186 | Cl | Cl | $CF(CF_3)_2$ | $CH(CH_3)CH_2$ |
| A.1.187 | Cl | Cl | $CF(CF_3)_2$ | $CH(CH_3)(CH_2)_2$ |
| A.1.188 | Cl | Cl | $CF(CF_3)_2$ | $CH(CH_3)(CH_2)_3$ |
| A.1.189 | Cl | Cl | $CF(CF_3)_2$ | $CH(CH_3)(CH_2)_4$ |
| A.1.190 | Cl | Cl | $OCF_3$ | $C(CH_3)_2CH_2$ |
| A.1.191 | Cl | Cl | $OCF_3$ | $C(CH_3)_2(CH_2)_2$ |
| A.1.192 | Cl | Cl | $OCF_3$ | $C(CH_3)_2(CH_2)_3$ |
| A.1.193 | Cl | Cl | $OCF_3$ | $C(CH_3)_2(CH_2)_4$ |
| A.1.194 | Cl | Cl | $OCF_3$ | $CH(CH_3)$ |
| A.1.195 | Cl | Cl | $OCF_3$ | $CH(CH_3)CH_2$ |
| A.1.196 | Cl | Cl | $OCF_3$ | $CH(CH_3)(CH_2)_2$ |
| A.1.197 | Cl | Cl | $OCF_3$ | $CH(CH_3)(CH_2)_3$ |
| A.1.198 | Cl | Cl | $OCF_3$ | $CH(CH_3)(CH_2)_4$ |
| A.1.199 | Cl | Cl | $CF_3$ | $C(CH_3)_2CH_2$ |
| A.1.200 | Cl | Cl | $CF_3$ | $C(CH_3)_2(CH_2)_2$ |
| A.1.201 | Cl | Cl | $CF_3$ | $C(CH_3)_2(CH_2)_3$ |
| A.1.202 | Cl | Cl | $CF_3$ | $C(CH_3)_2(CH_2)_4$ |
| A.1.203 | Cl | Cl | $CF_3$ | $CH(CH_3)$ |
| A.1.204 | Cl | Cl | $CF_3$ | $CH(CH_3)CH_2$ |
| A.1.205 | Cl | Cl | $CF_3$ | $CH(CH_3)(CH_2)_2$ |
| A.1.206 | Cl | Cl | $CF_3$ | $CH(CH_3)(CH_2)_3$ |
| A.1.207 | Cl | Cl | $CF_3$ | $CH(CH_3)(CH_2)_4$ |
| A.1.208 | Cl | Cl | $CF_2CF_3$ | $C(CH_3)_2CH_2$ |
| A.1.209 | Cl | Cl | $CF_2CF_3$ | $C(CH_3)_2(CH_2)_2$ |
| A.1.210 | Cl | Cl | $CF_2CF_3$ | $C(CH_3)_2(CH_2)_3$ |
| A.1.211 | Cl | Cl | $CF_2CF_3$ | $C(CH_3)_2(CH_2)_4$ |
| A.1.212 | Cl | Cl | $CF_2CF_3$ | $CH(CH_3)$ |
| A.1.213 | Cl | Cl | $CF_2CF_3$ | $CH(CH_3)CH_2$ |
| A.1.214 | Cl | Cl | $CF_2CF_3$ | $CH(CH_3)(CH_2)_2$ |
| A.1.215 | Cl | Cl | $CF_2CF_3$ | $CH(CH_3)(CH_2)_3$ |
| A.1.216 | Cl | Cl | $CF_2CF_3$ | $CH(CH_3)(CH_2)_4$ |
| A.1.217 | Cl | Cl | $CH(CF_3)_2$ | $C(CH_3)_2CH_2$ |
| A.1.218 | Cl | Cl | $CH(CF_3)_2$ | $C(CH_3)_2(CH_2)_2$ |
| A.1.219 | Cl | Cl | $CH(CF_3)_2$ | $C(CH_3)_2(CH_2)_3$ |
| A.1.220 | Cl | Cl | $CH(CF_3)_2$ | $C(CH_3)_2(CH_2)_4$ |
| A.1.221 | Cl | Cl | $CH(CF_3)_2$ | $CH(CH_3)$ |
| A.1.222 | Cl | Cl | $CH(CF_3)_2$ | $CH(CH_3)CH_2$ |
| A.1.223 | Cl | Cl | $CH(CF_3)_2$ | $CH(CH_3)(CH_2)_2$ |
| A.1.224 | Cl | Cl | $CH(CF_3)_2$ | $CH(CH_3)(CH_2)_3$ |
| A.1.225 | Cl | Cl | $CH(CF_3)_2$ | $CH(CH_3)(CH_2)_4$ |
| A.1.226 | Cl | H | $CF(CF_3)_2$ | $C(CH_3)_2CH_2$ |
| A.1.227 | Cl | H | $CF(CF_3)_2$ | $C(CH_3)_2(CH_2)_2$ |
| A.1.228 | Cl | H | $CF(CF_3)_2$ | $C(CH_3)_2(CH_2)_3$ |
| A.1.229 | Cl | H | $CF(CF_3)_2$ | $C(CH_3)_2(CH_2)_4$ |
| A.1.230 | Cl | H | $CF(CF_3)_2$ | $CH(CH_3)$ |
| A.1.231 | Cl | H | $CF(CF_3)_2$ | $CH(CH_3)CH_2$ |
| A.1.232 | Cl | H | $CF(CF_3)_2$ | $CH(CH_3)(CH_2)_2$ |
| A.1.233 | Cl | H | $CF(CF_3)_2$ | $CH(CH_3)(CH_2)_3$ |
| A.1.234 | Cl | H | $CF(CF_3)_2$ | $CH(CH_3)(CH_2)_4$ |
| A.1.235 | Cl | H | $OCF_3$ | $C(CH_3)_2CH_2$ |
| A.1.236 | Cl | H | $OCF_3$ | $C(CH_3)_2(CH_2)_2$ |
| A.1.237 | Cl | H | $OCF_3$ | $C(CH_3)_2(CH_2)_3$ |
| A.1.238 | Cl | H | $OCF_3$ | $C(CH_3)_2(CH_2)_4$ |
| A.1.239 | Cl | H | $OCF_3$ | $CH(CH_3)$ |
| A.1.240 | Cl | H | $OCF_3$ | $CH(CH_3)CH_2$ |
| A.1.241 | Cl | H | $OCF_3$ | $CH(CH_3)(CH_2)_2$ |
| A.1.242 | Cl | H | $OCF_3$ | $CH(CH_3)(CH_2)_3$ |
| A.1.243 | Cl | H | $OCF_3$ | $CH(CH_3)(CH_2)_4$ |
| A.1.244 | Cl | H | $CF_3$ | $C(CH_3)_2CH_2$ |
| A.1.245 | Cl | H | $CF_3$ | $C(CH_3)_2(CH_2)_2$ |
| A.1.246 | Cl | H | $CF_3$ | $C(CH_3)_2(CH_2)_3$ |
| A.1.247 | Cl | H | $CF_3$ | $C(CH_3)_2(CH_2)_4$ |
| A.1.248 | Cl | H | $CF_3$ | $CH(CH_3)$ |
| A.1.249 | Cl | H | $CF_3$ | $CH(CH_3)CH_2$ |
| A.1.250 | Cl | H | $CF_3$ | $CH(CH_3)(CH_2)_2$ |
| A.1.251 | Cl | H | $CF_3$ | $CH(CH_3)(CH_2)_3$ |
| A.1.252 | Cl | H | $CF_3$ | $CH(CH_3)(CH_2)_4$ |
| A.1.253 | Cl | H | $CF_2CF_3$ | $C(CH_3)_2CH_2$ |
| A.1.254 | Cl | H | $CF_2CF_3$ | $C(CH_3)_2(CH_2)_2$ |
| A.1.255 | Cl | H | $CF_2CF_3$ | $C(CH_3)_2(CH_2)_3$ |
| A.1.256 | Cl | H | $CF_2CF_3$ | $C(CH_3)_2(CH_2)_4$ |
| A.1.257 | Cl | H | $CF_2CF_3$ | $CH(CH_3)$ |
| A.1.258 | Cl | H | $CF_2CF_3$ | $CH(CH_3)CH_2$ |
| A.1.259 | Cl | H | $CF_2CF_3$ | $CH(CH_3)(CH_2)_2$ |
| A.1.260 | Cl | H | $CF_2CF_3$ | $CH(CH_3)(CH_2)_3$ |
| A.1.261 | Cl | H | $CF_2CF_3$ | $CH(CH_3)(CH_2)_4$ |
| A.1.262 | Cl | H | $CH(CF_3)_2$ | $C(CH_3)_2CH_2$ |
| A.1.263 | Cl | H | $CH(CF_3)_2$ | $C(CH_3)_2(CH_2)_2$ |
| A.1.264 | Cl | H | $CH(CF_3)_2$ | $C(CH_3)_2(CH_2)_3$ |
| A.1.265 | Cl | H | $CH(CF_3)_2$ | $C(CH_3)_2(CH_2)_4$ |
| A.1.266 | Cl | H | $CH(CF_3)_2$ | $CH(CH_3)$ |
| A.1.267 | Cl | H | $CH(CF_3)_2$ | $CH(CH_3)CH_2$ |
| A.1.268 | Cl | H | $CH(CF_3)_2$ | $CH(CH_3)(CH_2)_2$ |
| A.1.269 | Cl | H | $CH(CF_3)_2$ | $CH(CH_3)(CH_2)_3$ |
| A.1.270 | Cl | H | $CH(CF_3)_2$ | $CH(CH_3)(CH_2)_4$ |

TABLE 1

This table discloses the 270 compounds T1.1.1 to T1.1.270 of the formula (T1)

in which, for each of these 270 specific compounds, each of the of the variables $R_1$, $S_1$, $S_3$ and $Y_1$ has the specific meaning given in the corresponding line, appropriately selected from the 270 lines A.1.1 to A.1.270, of the Table A.

For example, the specific compound T1.1.23 is the compound of the formula T1, in which each of the of the variables $R_1$, $S_1$, $S_3$ and $Y_1$ has the specific meaning given in the line A.1.23 of the Table A. According to the same system, also all of the other 269 specific compounds disclosed in the Table 1 as well as all of the specific compounds disclosed in the Tables 2 to 63 are specified analogously.

TABLE 2

This table discloses the 270 compounds T2.1.1 to T2.1.270 of the formula (T2)

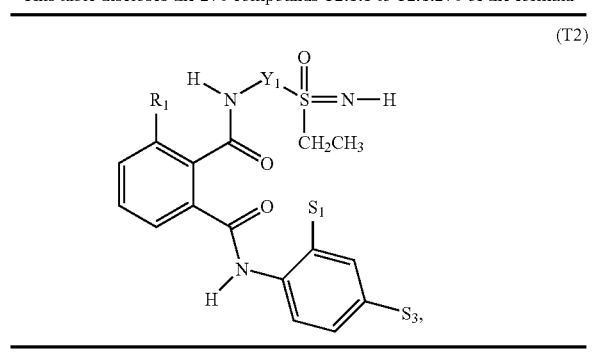

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 3

This table discloses the 270 compounds T3.1.1 to T3.1.270 of the formula (T3)

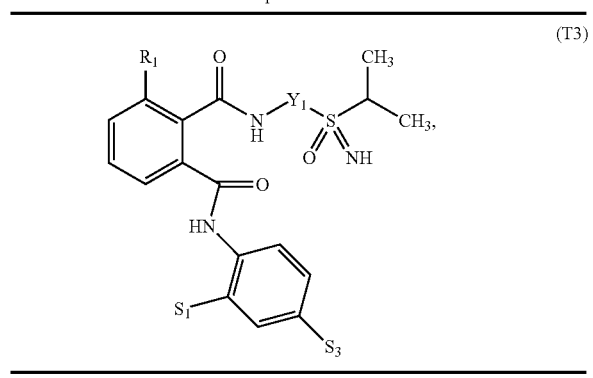

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 4

This table discloses the 270 compounds T4.1.1 to T4.1.270 of the formula (T4)

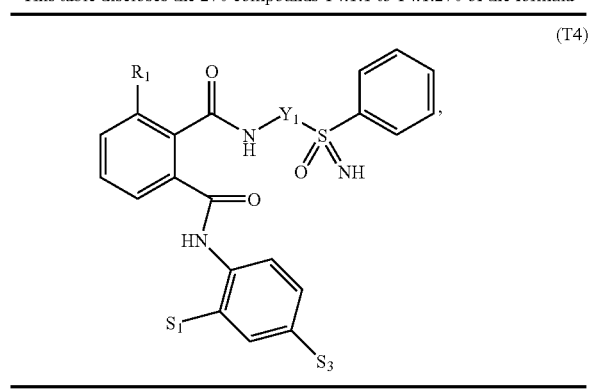

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 5

This table discloses the 270 compounds T5.1.1 to T5.1.270 of the formula (T5)

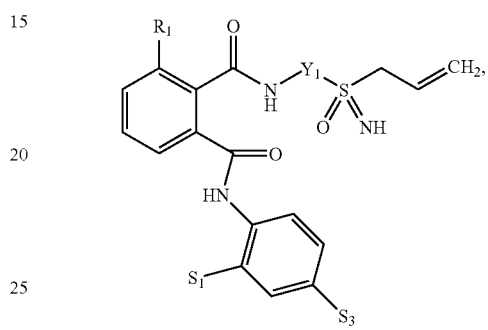

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 6

This table discloses the 270 compounds T6.1.1 to T6.1.270 of the formula (T6)

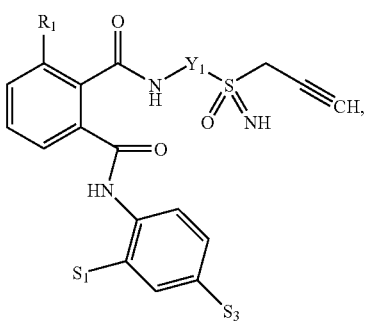

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 7

This table discloses the 270 compounds T7.1.1 to T7.1.270 of the formula (T7)

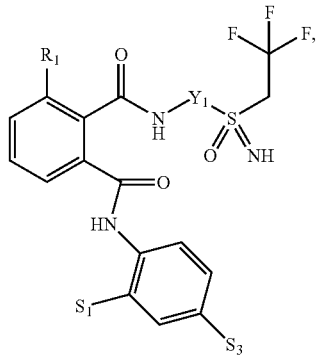

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 8

This table discloses the 270 compounds T8.1.1 to T8.1.270 of the formula (T8)

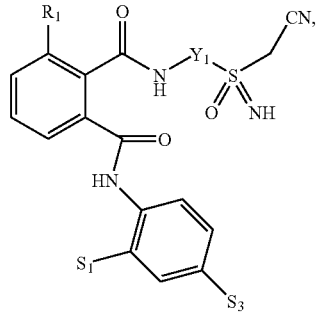

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 9

This table discloses the 270 compounds T9.1.1 to T9.1.270 of the formula (T9)

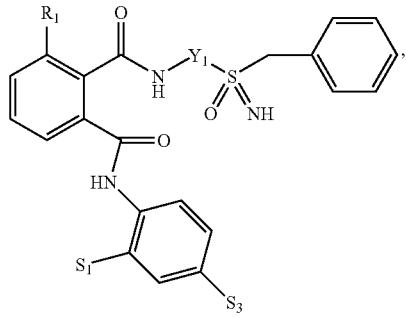

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 10

This table discloses the 270 compounds T10.1.1 to T10.1.270 of the formula (T10)

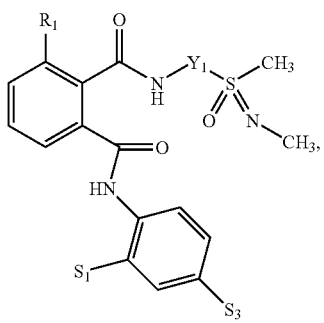

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 11

This table discloses the 270 compounds T11.1.1 to T11.1.270 of the formula (T11)

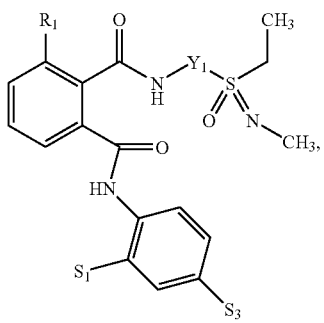

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 12

This table discloses the 270 compounds T12.1.1 to T12.1.270 of the formula

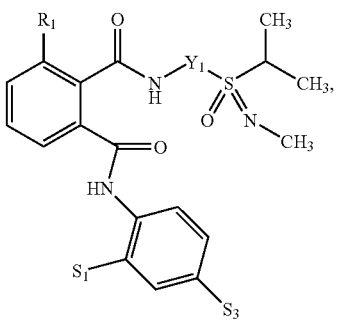

(T12)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 13

This table discloses the 270 compounds T13.1.1 to T13.1.270 of the formula

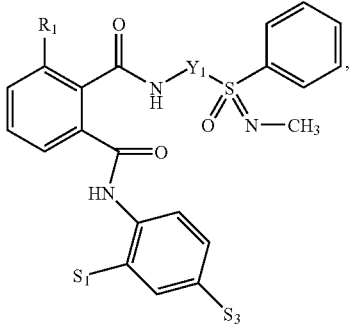

(T13)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 14

This table discloses the 270 compounds T14.1.1 to T14.1.270 of the formula

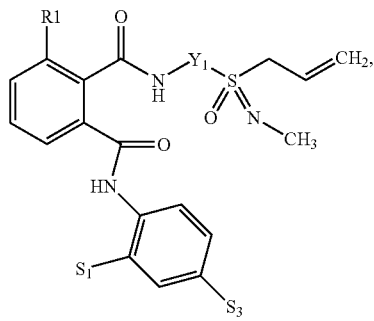

(T14)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 15

This table discloses the 270 compounds T15.1.1 to T15.1.270 of the formula

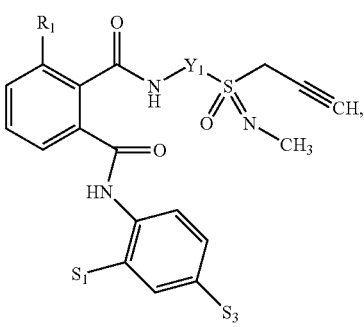

(T15)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 16

This table discloses the 270 compounds T16.1.1 to T16.1.270 of the formula

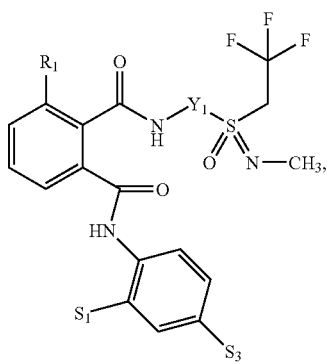

(T16)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 17

This table discloses the 270 compounds
T17.1.1 to T17.1.270 of the formula

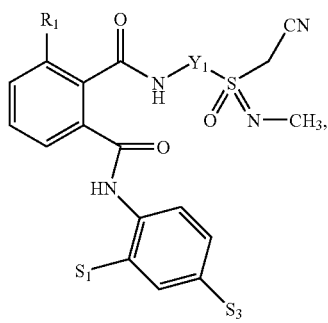

(T17)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 18

This table discloses the 270 compounds
T18.1.1 to T18.1.270 of the formula

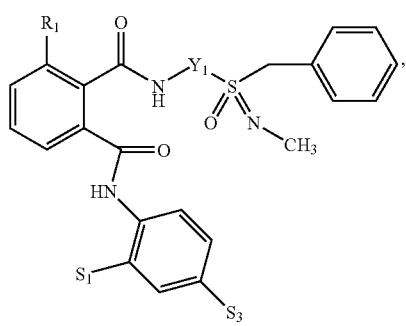

(T18)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 19

This table discloses the 270 compounds
T19.1.1 to T19.1.270 of the formula

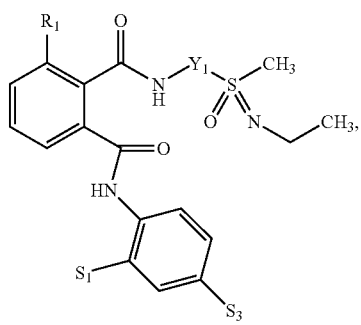

(T19)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 20

This table discloses the 270 compounds
T20.1.1 to T20.1.270 of the formula

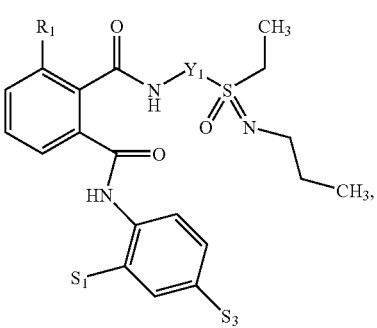

(T20)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 21

This table discloses the 270 compounds
T21.1.1 to T21.1.270 of the formula

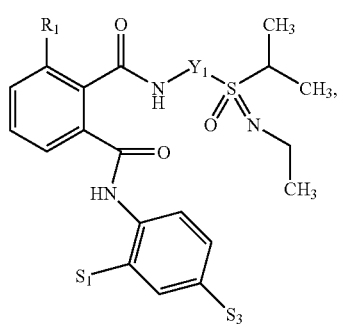

(T21)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 22

This table discloses the 270 compounds
T22.1.1 to T22.1.270 of the formula (T22)

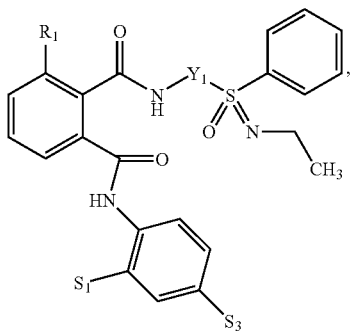

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 23

This table discloses the 270 compounds
T23.1.1 to T23.1.270 of the formula (T23)

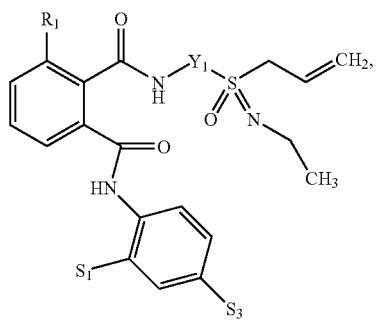

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 24

This table discloses the 270 compounds
T24.1.1 to T24.1.270 of the formula (T24)

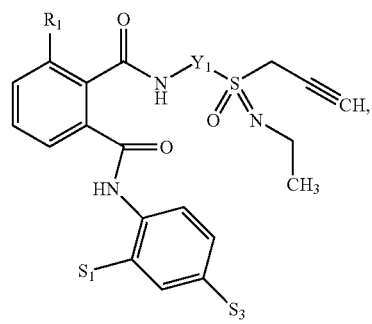

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 25

This table discloses the 270 compounds
T25.1.1 to T25.1.270 of the formula (T25)

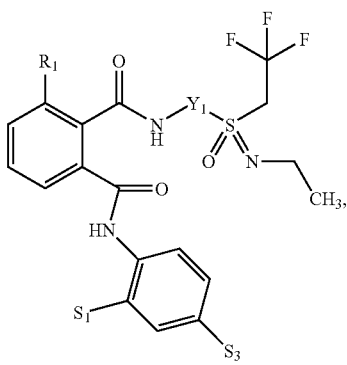

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 26

This table discloses the 270 compounds
T26.1.1 to T26.1.270 of the formula (T26)

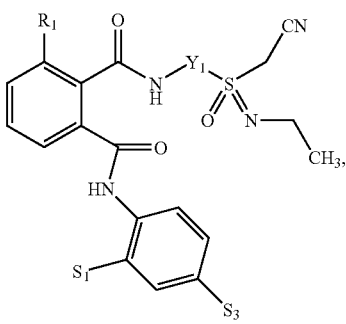

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 27

This table discloses the 270 compounds
T27.1.1 to T27.1.270 of the formula

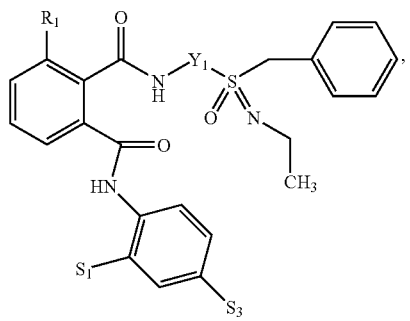
(T27)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 28

This table discloses the 270 compounds
T28.1.1 to T28.1.270 of the formula

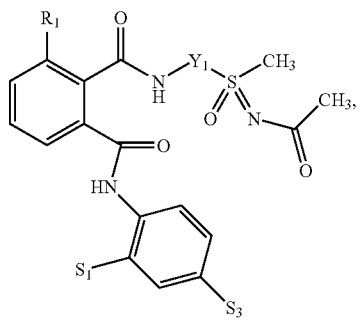
(T28)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 29

This table discloses the 270 compounds
T29.1.1 to T29.1.270 of the formula

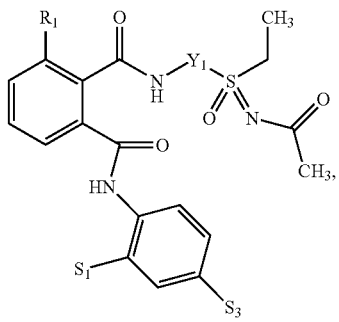
(T29)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 30

This table discloses the 270 compounds
T30.1.1 to T30.1.270 of the formula

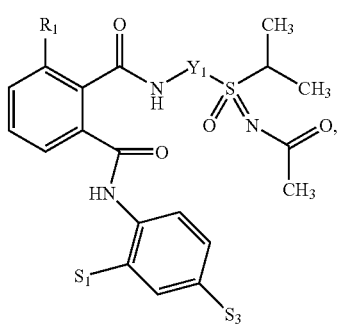
(T30)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 31

This table discloses the 270 compounds
T31.1.1 to T31.1.270 of the formula

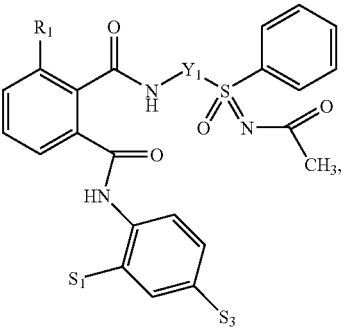
(T31)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 32

This table discloses the 270 compounds
T32.1.1 to T32.1.270 of the formula

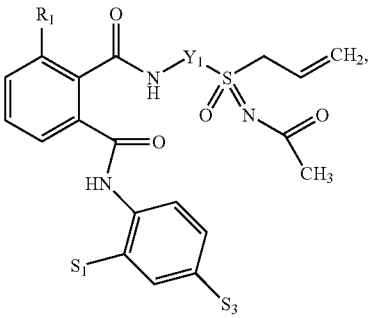
(T32)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 33

This table discloses the 270 compounds
T33.1.1 to T33.1.270 of the formula

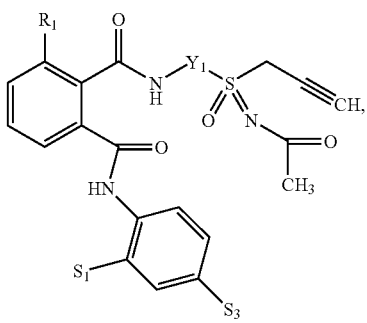
(T33)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 34

This table discloses the 270 compounds
T34.1.1 to T34.1.270 of the formula

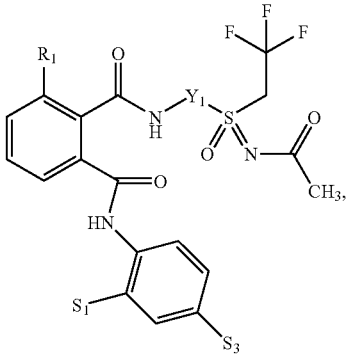
(T34)

in which, for each of these 270 specific compounds, each of the variables $R_1$, S1, S3 and $Y_1$ has the specific meaning given in the corresponding line, appropriately selected from the 270 lines A.1.1 to A.1.270, of the Table A.

TABLE 35

This table discloses the 270 compounds T35.1.1 to
T35.1.270 of the formula

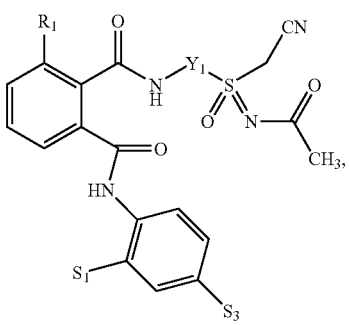
(T35)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 36

This table discloses the 270 compounds T36.1.1 to
T36.1.270 of the formula

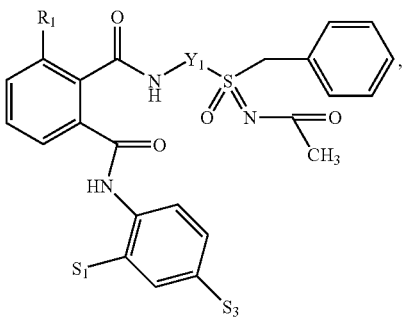
(T36)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 37

This table discloses the 270 compounds T37.1.1 to T37.1.270 of the formula

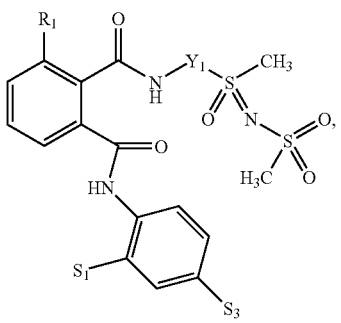

(T37)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 38

This table discloses the 270 compounds T38.1.1 to T38.1.270 of the formula

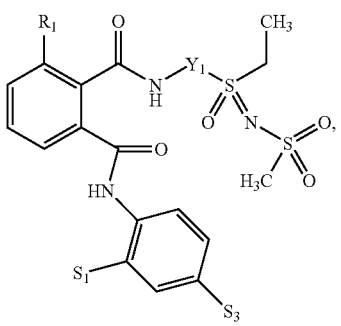

(T38)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 39

This table discloses the 270 compounds T39.1.1 to T39.1.270 of the formula

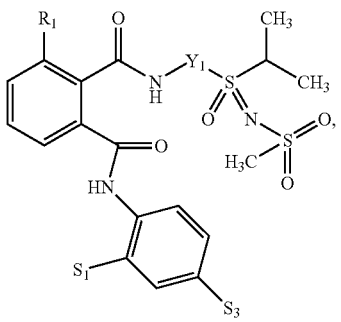

(T39)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 40

This table discloses the 270 compounds T40.1.1 to T40.1.270 of the formula

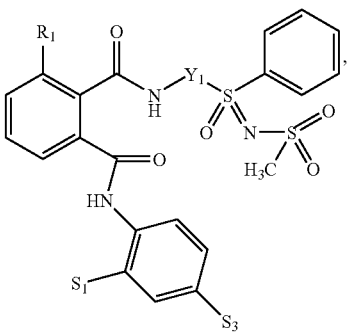

(T40)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 41

This table discloses the 270 compounds T41.1.1 to T41.1.270 of the formula

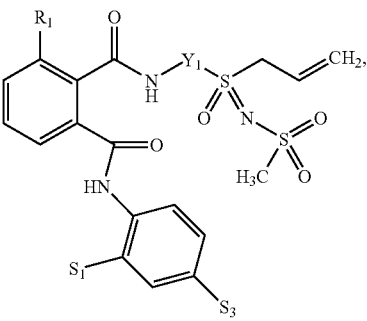

(T41)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 42

This table discloses the 270 compounds T42.1.1 to T42.1.270 of the formula

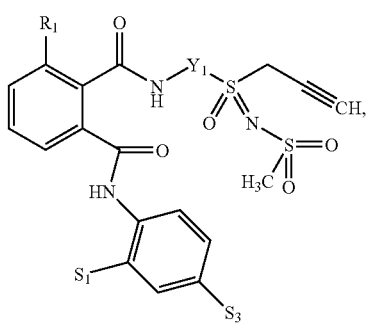

(T42)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 43

This table discloses the 270 compounds T43.1.1 to T43.1.270 of the formula (T43)

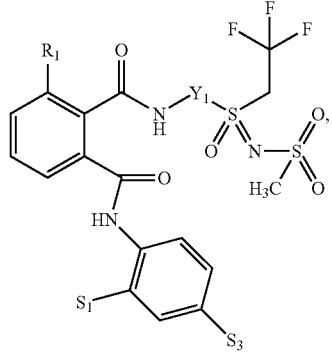

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 44

This table discloses the 270 compounds T44.1.1 to T44.1.270 of the formula (T44)

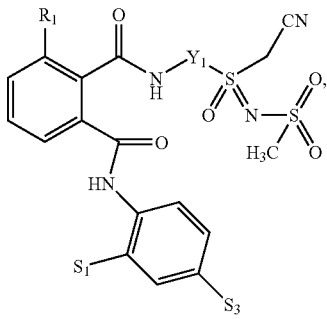

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 45

This table discloses the 270 compounds T45.1.1 to T45.1.270 of the formula (T45)

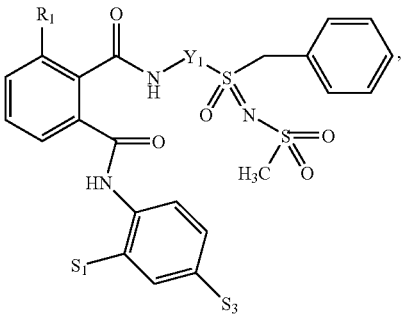

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 46

This table discloses the 270 compounds T46.1.1 to T46.1.270 of the formula (T46)

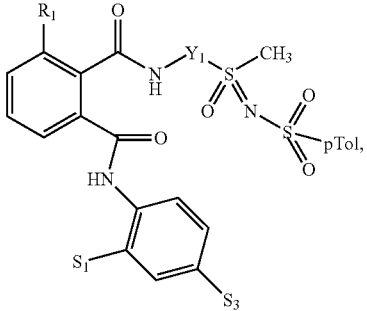

TABLE 47

This table discloses the 270 compounds T47.1.1 to T47.1.270 of the formula (T47)

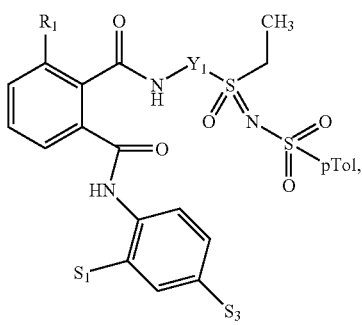

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A. pTol is para-toluene.

TABLE 48

This table discloses the 270 compounds T48.1.1 to T48.1.270 of the formula (T48)

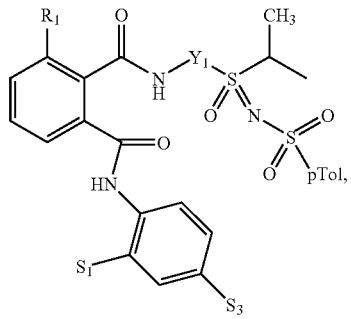

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A. pTol is para-toluene.

TABLE 49

This table discloses the 270 compounds T49.1.1 to T49.1.270 of the formula (T49)

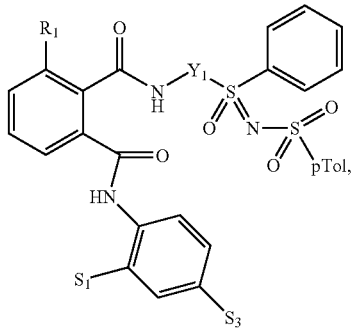

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A. pTol is para-toluene.

TABLE 50

This table discloses the 270 compounds T50.1.1 to T50.1.270 of the formula (T50)

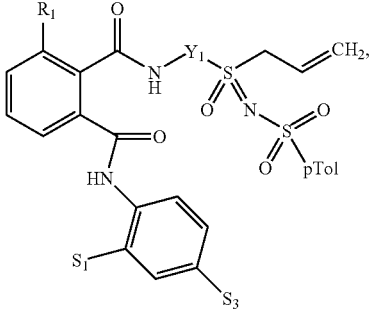

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A. pTol is para-toluene.

TABLE 51

This table discloses the 270 compounds T51.1.1 to T51.1.270 of the formula (T51)

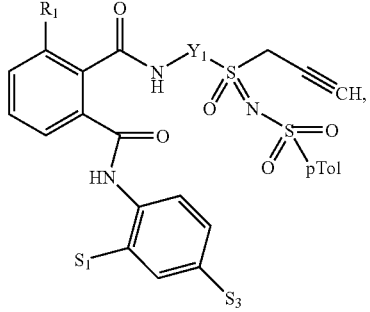

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A. pTol is para-toluene.

TABLE 52

This table discloses the 270 compounds T52.1.1 to T52.1.270 of the formula

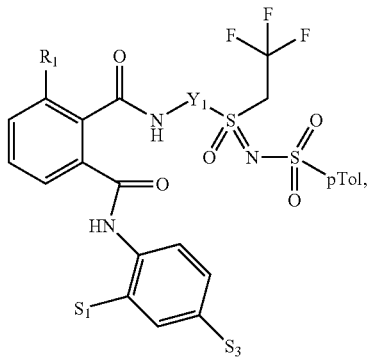

(T52)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A. pTol is para-toluene.

TABLE 53

This table discloses the 270 compounds T53.1.1 to T53.1.270 of the formula

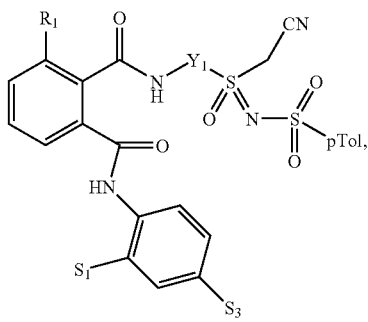

(T53)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A. pTol is para-toluene.

TABLE 54

This table discloses the 270 compounds T54.1.1 to T54.1.270 of the formula

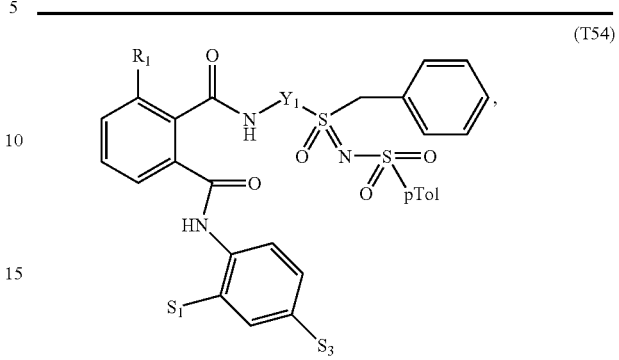

(T54)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A. pTol is para-toluene.

TABLE 55

This table discloses the 270 compounds T55.1.1 to T55.1.270 of the formula

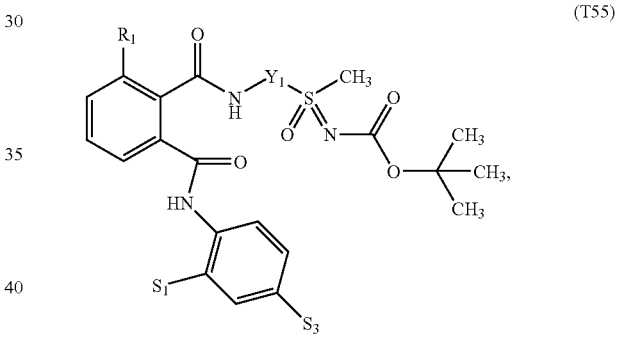

(T55)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 56

This table discloses the 270 compounds T56.1.1 to T56.1.270 of the formula

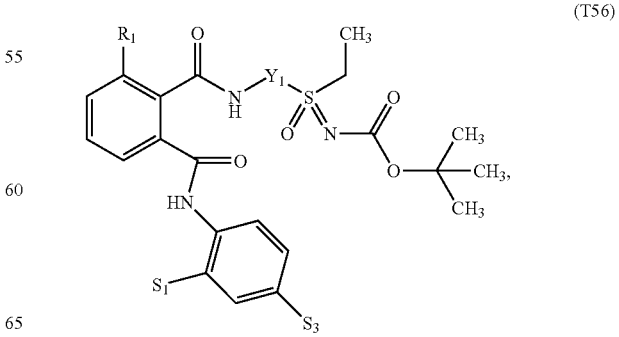

(T56)

TABLE 57

This table discloses the 270 compounds T57.1.1 to T57.1.270 of the formula (T57)

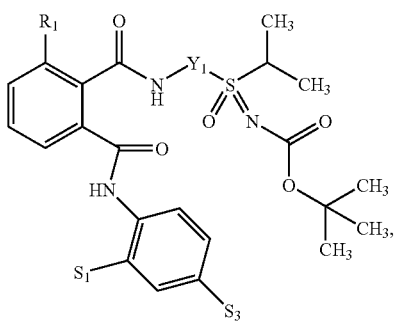

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 58

This table discloses the 270 compounds T58.1.1 to T58.1.270 of the formula (T58)

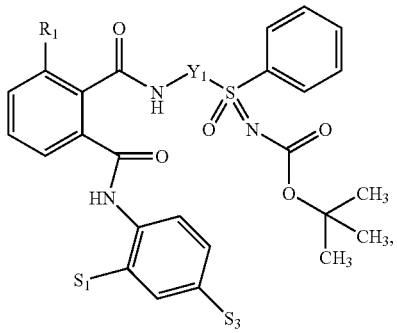

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 59

This table discloses the 270 compounds T59.1.1 to T59.1.270 of the formula (T59)

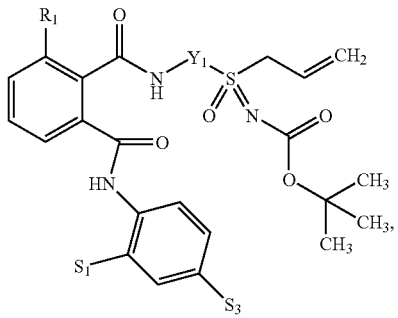

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 60

This table discloses the 270 compounds T60.1.1 to T60.1.270 of the formula (T60)

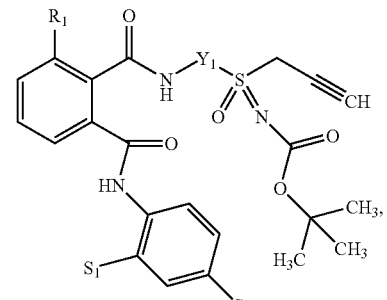

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 61

This table discloses the 270 compounds T61.1.1 to T61.1.270 of the formula

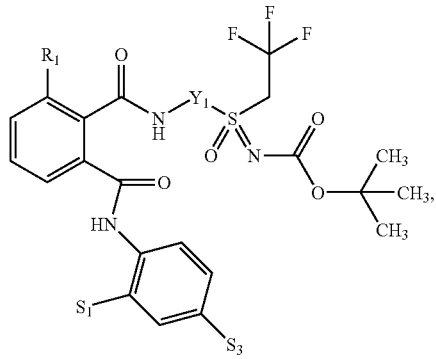

(T61)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 62

This table discloses the 270 compounds T62.1.1 to T62.1.270 of the formula

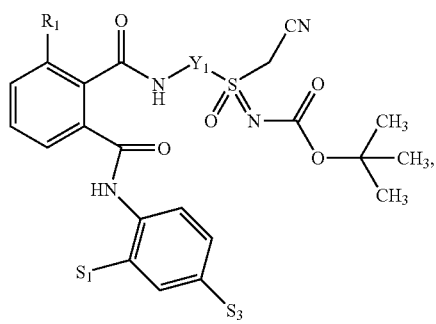

(T62)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 63

This table discloses the 270 compounds T63.1.1 to T63.1.270 of the formula

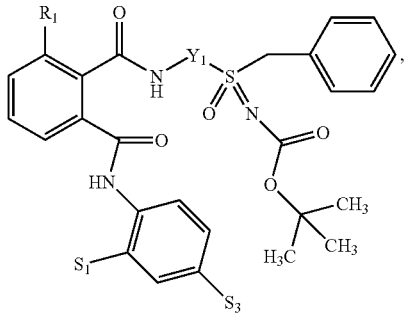

(T63)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

TABLE 64

This table discloses the 270 compounds T64.1.1 to T64.1.270 of the formula

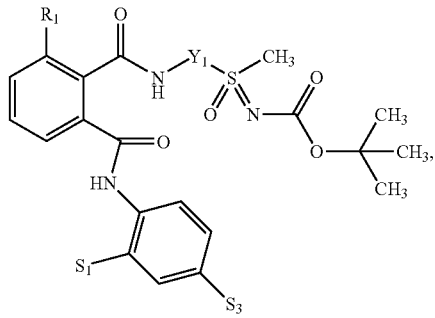

(T64)

in which, for each of these 270 specific compounds, each of the variables $R_1$, $S_1$, $S_3$ and $Y_1$ has the specific meaning given in the corresponding line, appropriately selected from the 270 lines A.1.1 to A.1.270, of the Table A.

Formulation Examples (%=Percent by Weight)

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2:Solutions | | | | |
|---|---|---|---|---|
| | a) | b) | c) | d) |
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | | | | |
|---|---|---|---|---|
| | a) | b) | c) | d) |
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | | |
|---|---|---|
| | a) | b) |
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | | | |
|---|---|---|---|
| | a) | b) | c) |
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

| Example F6: Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

| Example F7: Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

| Example F8: Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Biological Examples (%=Percent by Weight, Unless Otherwise Specified)

Example B1

Activity Against *Aphis craccivora*

Pea seedlings are infected with *Aphis craccivora*, subsequently sprayed with a spray mixture comprising 400 ppm of active ingredient and then incubated at 20°. 3 and 6 days later, the percentage reduction in the population (% activity) is determined by comparing the number of dead aphids between the treated and untreated plants.

In this test, compounds listed in the Tables above show good activity.

Example B2

Activity Against *Diabrotica balteata*

Maize seedlings are sprayed with an aqueous emulsion spray mixture comprising 400 ppm of active ingredient and, after the spray coating has dried on, populated with 10 larvae (2nd instar) of *Diabrotica balteata* and introduced into a plastic container. 6 days later, the percentage reduction in the population (% activity) is determined by comparing the number of dead larvae between the treated and untreated plants.

In this test, compounds listed in the Tables above show good activity. In particular, the compounds T.64.1.136, T64.1.1 and T1.1.1 have an activity of over 80%.

Example B3

Activity Against *Heliothis virescens* (Foliar Application)

Young soya plants are sprayed with an aqueous emulsion spray mixture comprising 400 ppm of active ingredient and, after the spray coating has dried on, populated with 10 caterpillars (1st instar) of *Heliothis virescens* and introduced into a plastic container. 6 days later, the percentage reduction in the population and in the feeding damage (% activity) are determined by comparing the number of dead caterpillars and the feeding damage between the treated and untreated plants.

In this test, compounds listed in the Tables above show good activity. In particular, the compounds T.64.1.136, T55.1.136, T1.1.136, T64.1.1, T1.1.1, T55.1.1 have an activity of over 80%.

Example B4

Activity Against *Heliothis virescens* (Application to Eggs)

*Heliothis virescens* eggs, which have been deposited on cotton, are sprayed with an aqueous emulsion spray mixture comprising 400 ppm of active ingredient. After 8 days, the percentage hatching rate of the eggs and the survival rate of the caterpillars (% activity) are evaluated in comparison with untreated control batches.

In this test, compounds listed in the Tables above show good activity. In particular, the compounds T.64.1.136, T55.1.136, T1.1.136, T64.1.1, T1.1.1, T55.1.1 have an activity of over 80%.

Example B5

Activity Against *Myzus persicae* (Foliar Application)

Pea seedlings are infected with *Myzus persicae*, subsequently sprayed with a spray mixture comprising 400 ppm of active ingredient and then incubated at 20°. 3 and 6 days later, the percentage reduction in the population (% activity) is determined by comparing the number of dead aphids between the treated and untreated plants.

In this test, compounds listed in the Tables above show good activity.

Example B6

Activity Against *Myzus persicae* (Systemic Application)

Pea seedlings are infected with *Myzus persicae*, and their roots are subsequently placed into a spray mixture comprising 400 ppm of active ingredient. The seedlings are then incubated at 20°. 3 and 6 days later, the percentage reduction in the population (% activity) is determined by comparing the number of dead aphids between the treated and untreated plants.

In this test, compounds listed in the Tables above show good activity.

Example B7

Activity Against *Plutella xylostella*

Young cabbage plants are sprayed with an aqueous emulsion spray mixture comprising 400 ppm of active ingredient and, after the spray coating has dried on, populated with 10 caterpillars (3rd instar) of *Plutella xylostella* and introduced into a plastic container. 3 days later, the percentage reduction in the population and in the feeding damage (% activity) are determined by comparing the number of dead caterpillars and the feeding damage between the treated and untreated plants.

In this test, compounds listed in the Tables above show good activity. In particular, the compounds T.64.1.136, T55.1.136, T1.1.136, T64.1.1, T1.1.1, T55.1.1 have an activity of over 80%.

Example B8

Activity Against *Spodoptera littoralis*

Young soya plants are sprayed with an aqueous emulsion spray mixture comprising 400 ppm of active ingredient and, after the spray coating has dried on, populated with 10 caterpillars (1st instar) of *Spodoptera littoralis* and introduced into a plastic container. 3 days later, the percentage reduction in the population and in the feeding damage (% activity) are determined by comparing the number of dead caterpillars and the feeding damage between the treated and untreated plants. In this test, compounds listed in the Tables above show good activity. In particular, the compounds T.64.1.136, T1.1.136, T64.1.1 and T1.1.1 have an activity of over 80%.

Example B9

Comparison of the Insecticidal Activity of Compounds According to the Invention with the Structurally Most Closely Comparable Compound From the State of the Art (Compound No. 124 Described on Page 23 of EP-A-1006107)

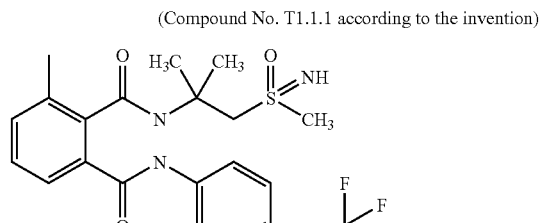

(Compound No. T1.1.1 according to the invention)

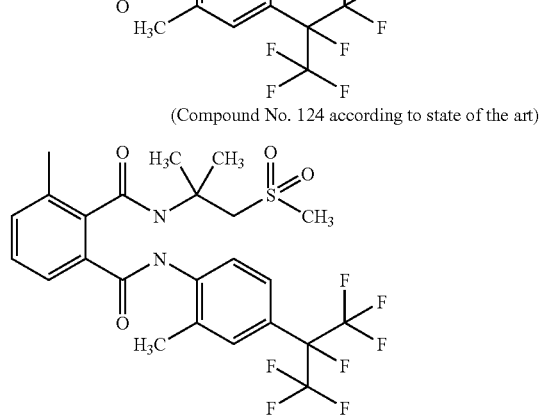

(Compound No. 124 according to state of the art)

Four day old maize seedlings (*Zea mais*, variety Stoneville) are placed individual in vials containing 24 ml water into which the chemical is diluted at the prescribed concentrations (12.5, 3 and 0.8 ppm). Seedlings are allowed to grow for six days. Subsequently leaves are cut and placed in a Petri dish (3.5 cm diameter), inoculated with twelve to fifteen 1st instar

*S. littoralis* larvae and incubated for four days in a growth chamber (25° C., 50% r.h., 18:6 L:D photo period). Number of alive insects are counted and percentage of dead calculated. Tests were conducted with one replicate. Results are shown in Table B9:

TABLE B9

Systemic Insecticide Test for *Spodoptera littoralis* (Lepidoptera:Noctuidae):

| Compound: | Concentration (ppm) | Death rate (%) after 4 days |
|---|---|---|
| Comp. 124 (state of the art) | 12.5 | 90 |
| Comp. 124 (state of the art) | 3 | 20 |
| Comp. 124 (state of the art) | 0.8 | 0 |
| Comp. T1.1.1 (invention) | 12.5 | 100 |
| Comp. T1.1.1 (invention) | 3 | 100 |
| Comp. T1.1.1 (invention) | 0.8 | 100 |

Table B9 shows that compound No. T1.1.1 according to the invention exerts a substantially better insecticidal action on *Spodoptera littoralis* than the compound from the state of the art. Especially at low application rates (3 and 0.8 ppm) the compound according to the invention is far superior to the compound of the state of the art. This enhanced effect was not to be expected on the basis of the structural similarity of these compounds.

What is claimed is:

1. A compound of formula I

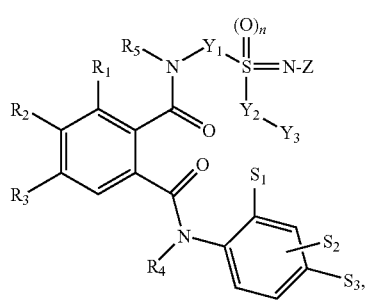

wherein
n is 0 or 1;
$R_1$ is halogen, cyano, $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylsulfonyloxy, $C_1$-$C_8$haloalkylsulfonyloxy or —$OSO_2F$;
each of $R_2$ and $R_3$, which may be the same or different, represents hydrogen, halogen, cyano, $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylsulfonyloxy, $C_1$-$C_8$haloalkylsulfonyloxy, —$OSO_2F$;
or $R_2$ together with $R_3$ form a $C_2$-$C_6$alkylene or $C_3$-$C_6$alkenylene bridge which may be interrupted by nitrogene, oxygene and/or —C(O)—, or by —S(O)$_m$—; and said bridge may be mono- or poly-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, amino, hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano, nitro and/or phenyl, it being possible for the phenyl group in turn to be substituted by hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano or nitro, and the substituents at the nitrogen atom in said bridge being other than halogen, and two oxygen atoms not being located next to one another;
m is 0, 1 or 2;
each of $S_1$ and $S_2$, which may be the same or different, represents hydrogen, halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkenyl, $C_2$-$C_8$haloalkenyl, $C_1$-$C_8$alkynyl, $C_2$-$C_8$haloalkynyl, $C_3$-$C_6$cycloalkyl, $C_3$-$C_6$halocycloalkyl, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_6$alkylamino or di-($C_1$-$C_6$alkyl)amino, whose $C_1$-$C_6$alkyl groups may be the same or different;
$S_3$ is cyano, $C_1$-$C_6$alkyl, halo-$C_1$-$C_6$alkyl, $C_1$-$C_6$alkoxy, halo-$C_1$-$C_6$alkoxy, halo-$C_1$-$C_6$alkoxyhalo-$C_1$-$C_6$alkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl or $C_1$-$C_8$haloalkylsulfonyl; or
$S_3$ is a three- to ten-membered monocyclic or fused bicyclic ring system which can be aromatic, partially saturated or fully saturated and can contain 1 to 4 hetero atoms selected from the group consisting of nitrogen, oxygen and sulfur, the ring system being bonded to the phenyl ring directly or via a —O—, —S—, $C_1$-$C_4$alkylene, —CH=CH—, —C≡C—, —$CH_2O$—, —$CH_2N$($C_1$-$C_4$alkyl)-, —$CH_2SO$—, or —$CH_2SO_2$ group and it not being possible for each ring system to contain more than 2 oxygen atoms and not more than 2 sulfur atoms, and it being possible for the ring system itself to be mono-, di- or trisubstituted by $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di-($C_1$-$C_2$alkyl)aminosulfonyl, di-($C_1$-$C_4$alkyl)amino, halogen, cyano, nitro, phenyl and benzylthio, it being possible for phenyl and benzylthio, in turn, to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or nitro, and substituents on the nitrogen in the heterocyclic ring being other than halogen;

each of $R_4$ and $R_5$, which may be the same or different, represents hydrogen, $C_1$-$C_6$alkyl, $C_3$-$C_6$alkenyl or $C_3$-$C_6$alkynyl;

$Y_1$ is a $C_1$-$C_6$alkylene, $C_2$-$C_6$alkenylene or $C_3$-$C_6$alkynylene chain which may be mono-, di- or trisubstituted by $R_9$, where the unsaturated bonds of the chain are not attached directly to the sulfur atom; or is $C_3$-$C_6$cycloalkylene, which may be mono-, di- or trisubstituted by $R_{10}$;

$R_9$ and $R_{10}$ independently of one another are halogen, nitro, cyano, hydroxy, $C_1$-$C_6$alkyl, $C_1$-$C_6$haloalkyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkoxycarbonyl, $C_1$-$C_6$alkylcarbonyl, $C_1$-$C_6$alkoxy-$C_1$-$C_6$alkyl, $C_1$-$C_6$alkoxy-$C_1$-$C_6$alkyl, $C_1$-$C_6$alkoxy, $C_1$-$C_6$halo-alkoxy, benzyl or phenyl, where phenyl and benzyl for their part may be mono- or polysubstituted by $C_1$-$C_6$alkyl, $C_1$-$C_6$haloalkyl, $C_1$-$C_6$alkoxy, $C_1$-$C_6$haloalkoxy, halogen, cyano, hydroxyl or nitro;

$Y_2$ is a $C_1$-$C_6$alkylene, $C_2$-$C_6$alkenylene or $C_3$-$C_6$alkynylene chain which may be mono-, di- or trisubstituted by $R_{11}$, where the unsaturated bonds of the chain are not attached directly to the sulfur atom; or is $C_3$-$C_6$cycloalkylene, which may be mono-, di- or trisubstituted by $R_{12}$;

$R_{11}$ and $R_{12}$ independently of one another are halogen, nitro, cyano, hydroxy, $C_1$-$C_6$alkyl, $C_1$-$C_6$haloalkyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkoxycarbonyl, $C_1$-$C_6$alkylcarbonyl, $C_1$-$C_6$alkoxy-$C_1$-$C_6$alkyl, $C_1$-$C_6$alkoxy-$C_1$-$C_6$alkyl, $C_1$-$C_6$alkoxy, $C_1$-$C_6$halo-alkoxy, benzyl or phenyl, where phenyl and benzyl for their part may be mono-, di- or trisubstituted by $C_1$-$C_6$alkyl, $C_1$-$C_6$haloalkyl, $C_1$-$C_6$alkoxy, $C_1$-$C_6$haloalkoxy, halogen, cyano, hydroxyl or nitro;

$Y_3$ is hydrogen or $C_1$-$C_6$alkyl;

Z is hydrogen, $C_1$-$C_6$alkyl, $C_1$-$C_6$haloalkyl, $C_1$-$C_6$cycloalkyl, $C_1$-$C_6$halocycloalkyl, $C_1$-$C_6$alkylthio, $C_1$-$C_6$haloalkylthio or $C_1$-$C_6$alkoxy-$C_1$-$C_6$alkyl; or $C_1$-$C_6$alkyl, $C_1$-$C_6$haloalkyl, $C_1$-$C_6$cycloalkyl, $C_1$-$C_6$halocycloalkyl, $C_1$-$C_6$alkylthio, $C_1$-$C_6$haloalkylthio or $C_1$-$C_6$alkoxy-$C_1$-$C_6$alkyl substituted by $C_1$-$C_6$alkyl, $C_1$-$C_6$haloalkyl, $C_1$-$C_6$cycloalkyl, $C_1$-$C_6$halocycloalkyl, $C_1$-$C_6$alkoxy, or $C_1$-$C_6$haloalkoxy; or Z is —C(O)$R_6$, —C(O)O—$R_7$, —CONR$_{13}$R$_{14}$, —SO$_2$R$_{15}$ or —OP(OR$_{16}$)(OR$_{17}$)—OR$_{18}$;

$R_6$ is $C_1$-$C_6$alkyl, $C_1$-$C_6$haloalkyl, $C_1$-$C_6$cycloalkyl, $C_1$-$C_6$halocycloalkyl, $C_1$-$C_6$alkylthio, $C_1$-$C_6$haloalkylthio, $C_1$-$C_6$alkoxycarbonyl, $C_1$-$C_6$alkylcarbonyl or $C_1$-$C_6$alkoxy-$C_1$-$C_6$alkyl; or $C_1$-$C_6$alkyl, $C_1$-$C_6$haloalkyl, $C_1$-$C_6$cycloalkyl, $C_1$-$C_6$halocycloalkyl, $C_1$-$C_6$alkylthio, $C_1$-$C_6$haloalkylthio, $C_1$-$C_6$alkoxycarbonyl, $C_1$-$C_6$alkylcarbonyl or $C_1$-$C_6$alkoxy-$C_1$-$C_6$alkyl substituted by $C_1$-$C_6$alkyl, $C_1$-$C_6$haloalkyl, $C_1$-$C_6$cycloalkyl, $C_1$-$C_6$halocycloalkyl, $C_1$-$C_6$alkoxy, or $C_1$-$C_6$haloalkoxy; $R_7$, $R_{13}$, $R_{14}$, $R_{15}$, $R_{16}$, $R_{17}$ and $R_{18}$ independently of one another are $C_1$-$C_6$alkyl, $C_1$-$C_6$haloalkyl, $C_1$-$C_6$cycloalkyl or $C_1$-$C_6$halocycloalkyl; or $C_1$-$C_6$alkyl, $C_1$-$C_6$haloalkyl, $C_1$-$C_6$cycloalkyl or $C_1$-$C_6$halocycloalkyl substituted by $C_1$-$C_6$alkyl, $C_1$-$C_6$haloalkyl, $C_1$-$C_6$cycloalkyl, $C_1$-$C_6$halocycloalkyl, $C_1$-$C_6$alkoxy or $C_1$-$C_6$haloalkoxy; and agronomically acceptable salts/isomers/enantiomers/tautomers of those compounds.

2. A compound according to claim 1, wherein Z is hydrogen, —C(O)$R_6$, —C(O)O—$R_7$, —CONR$_{13}$R$_{14}$, —SO$_2$R$_{15}$ or —OP(OR$_{16}$)(OR$_{17}$)—OR$_{18}$.

3. A pesticidal composition, which comprises at least one compound according to claim 1 of the formula I or, where appropriate, a tautomer thereof, in each case in free form or in agrochemically utilizable salt form, as active ingredient and at least one auxiliary.

4. A composition according to claim 3 for controlling insects or representatives of the order Acarina.

5. A method for controlling pests, which comprises applying a composition according to claim 3 to the pests or their environment.

6. A method according to claim 5 for controlling insects or representatives of the order Acarina.

7. A method according to claim 5 for the protection of plant propagation material from the attack by pests, which comprises treating the propagation material or the site, where the propagation material is planted.

8. Plant propagation material treated in accordance with the method described in claim 7.

\* \* \* \* \*